(12) United States Patent
Freire et al.

(10) Patent No.: US 9,371,307 B2
(45) Date of Patent: Jun. 21, 2016

(54) SERINE PROTEASE INHIBITORS

(75) Inventors: Ernesto Freire, Baltimore, MD (US); Patrick C. Ross, College Park, MD (US); Rogelio Siles, Cockeysville, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 56 days.

(21) Appl. No.: 14/344,450

(22) PCT Filed: Sep. 12, 2012

(86) PCT No.: PCT/US2012/054775
§ 371 (c)(1),
(2), (4) Date: Dec. 5, 2014

(87) PCT Pub. No.: WO2013/039985
PCT Pub. Date: Mar. 21, 2013

(65) Prior Publication Data
US 2015/0080451 A1  Mar. 19, 2015

Related U.S. Application Data

(60) Provisional application No. 61/533,501, filed on Sep. 12, 2011.

(51) Int. Cl.
| | | |
|---|---|---|
| C07D 333/10 | (2006.01) |
| C07C 311/13 | (2006.01) |
| A61K 45/06 | (2006.01) |
| A61K 31/381 | (2006.01) |
| A61K 31/18 | (2006.01) |

(52) U.S. Cl.
CPC .............. *C07D 333/10* (2013.01); *A61K 31/18* (2013.01); *A61K 31/381* (2013.01); *A61K 45/06* (2013.01); *C07C 311/13* (2013.01)

(58) Field of Classification Search
None
See application file for complete search history.

(56) References Cited

U.S. PATENT DOCUMENTS

| 4,062,960 A | 12/1977 | Holland |
| 6,867,214 B1 | 3/2005 | Fukami |
| 7,071,220 B2 | 7/2006 | Satoh |
| 7,888,348 B2 | 2/2011 | Muto |

FOREIGN PATENT DOCUMENTS

| WO | 2002067865 A2 | 9/2002 |
| WO | 2004019935 A1 | 3/2004 |
| WO | 2004092117 A1 | 10/2004 |
| WO | 2004092130 A2 | 10/2004 |
| WO | 2005014597 A1 | 2/2005 |
| WO | 2007047432 A1 | 4/2007 |
| WO | 2008084004 A1 | 7/2008 |
| WO | 2009120783 A1 | 10/2009 |
| WO | WO2009120783 A1 * | 10/2009 |

OTHER PUBLICATIONS

Compound (CAS RN 1281688-87-6) entered CAS Chemical Library by supplier Enamine on Apr. 18, 2011.*
Schafer et al. Drug Discovery Today, 2008, 13 (21/22), 913-916.*
Horig et al. Journal of Translational Medicine 2004, 2(44).*
Harada et al (2001) Ethenesulfonamide and ethanesulfonamide derivatives, a novel class of orally active endothelin-A receptor antagonists. Bioorg Med Chem. Nov. 2001;9(11):2955-68.
Young et al (2007) Selective and dual action orally active inhibitors of thrombin and factor Xa. Bioorg Med Chem Lett. May 15, 2007;17(10):2927-30. Epub Mar. 30, 2007.
Takai et al (2010) Chymase as an important target for preventing complications of metabolic syndrome. Curr Med Chem. 2010;17(28):3223-9.
Trivedi et al (2010) Mast cell peptidases: chameleons of innate immunity and host defense. Am J Respir Cell Mol Biol. Mar. 2010;42(3):257-67. doi: 10.1165/rcmb.2009-0324RT. Epub Nov. 20, 2009.
Caughey et al (2007) Mast cell tryptases and chymases in inflammation and host defense. Immunol Rev. Jun. 2007;217:141-54.
Caughey et al (2011) Mast cell proteases as protective and inflammatory mediators. Adv Exp Med Biol. 2011;716:212-34. doi: 10.1007/978-1-4419-9533-9_12.
Takai et al (2004) Therapeutic applications of chymase inhibitors in cardiovascular diseases and fibrosis. Eur J Pharmacol. Oct. 6, 2004;501(1-3):1-8.
Matsumoto et al (2003) Chymase inhibition prevents cardiac fibrosis and improves diastolic dysfunction in the progression of heart failure. Circulation. May 27, 2003;107(20):2555-8. Epub May 12, 2003.
Jin et al (2002) Beneficial effects of cardiac chymase inhibition during the acute phase of myocardial infarction. Life Sci. Jun. 14, 2002;71(4):437-46.
Muto et al (2002) Recent chymase inhibitors and their effects in in vivo models. IDrugs. Dec. 2002;5(12):1141-50.
Akahoshi et al (2001) Synthesis, structure-activity relationships, and pharmacokinetic profiles of nonpeptidic difluoromethylene ketones as novel inhibitors of human chymase. J Med Chem. Apr. 12, 2001;44(8):1297-304.
Pereira et al (1999) The 2.2 A crystal structure of human chymase in complex with succinyl-Ala-Ala-Pro-Phe-chloromethylketone: structural explanation for its dipeptidyl carboxypeptidase specificity. J Mol Biol. Feb. 12, 1999;286 (1):163-73.

(Continued)

*Primary Examiner* — Yong Chu
(74) *Attorney, Agent, or Firm* — Ward and Smith, P.A.; Jeffrey W. Childers

(57) ABSTRACT

Potent low molecular weight, highly selective, competitive non-peptidic serine protease inhibitors and their use in treating serine protease-associated diseases are disclosed.

19 Claims, 4 Drawing Sheets

(56) References Cited

OTHER PUBLICATIONS

Hirayama F, "Design, synthesis and biological activity of YM-60828 derivatives: potent and orally-Bioavailable factor Xa inhibitors based on naphthoanilide and naphthalensulfonanilide templates", Bioorganic & Medicinal Chemistry, Aug. 1, 2002; vol. 10, Nr:8, pp. 2597-2610.

International Search Report dated Mar. 12, 2013 for corresponding PCT application No. PCT/US2012/054775.

* cited by examiner

SERINE PROTEASE INHIBITORS

REFERENCE TO RELATED APPLICATIONS

This application is a 35 U.S.C. §317 U.S. national phase entry of International Application No. PCT/US2012/054775 having an international filing date of Sep. 12, 2012, which claims the benefit of U.S. Provisional Application No. 61/533,501, filed Sep. 12, 2011, the content of each of the aforementioned applications is herein incorporated by reference in its entirety.

FEDERALLY SPONSORED RESEARCH OR DEVELOPMENT

This invention was made in part with United States Government support under GM57144 awarded by the National Institutes of Health (NIH). The U.S. Government has certain rights in the invention.

BACKGROUND

Chymase, a chymotrypsin-like serine protease, has been previously validated as an important target for drug development against cardiovascular disease. Chymase is stored as an inactive enzyme in the secretory granules of mast cells and is involved in the angiotensin-converting enzyme (ACE)-independent synthesis of angiotensin II (Ang II). This process occurs immediately after chymase is released into the interstitial tissues following vascular injury. It has been shown that chymase-positive cells accumulate in atherosclerotic lesions in patients and that chymase inhibition prevented the development of atherosclerosis in an animal model. Cardiac dysfunction after myocardial infarction also has been shown to be attenuated by chymase inhibition. Further, cardiac chymase has been shown to participate directly in the pathophysiologic state after myocardial infarction in hamsters. Inhibition of chymase also may be useful for preventing vascular proliferation in grafted vessels and in the repair of organs affected by stroke.

SUMMARY

In some aspects, the presently disclosed subject matter provides potent low-molecular weight, highly selective, competitive non-peptidic serine protease inhibitors. In certain aspects, the presently disclosed compounds inhibit chymase. The presently disclosed inhibitors comprise a novel chemical scaffold, which does not carry any of the chemical functionalities traditionally associated with serine protease inhibitors.

In particular aspects, the presently disclosed subject matter provides a compound of Formulae (I-III):

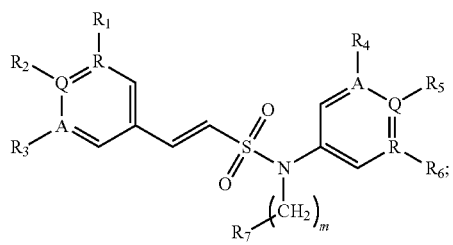

(I)

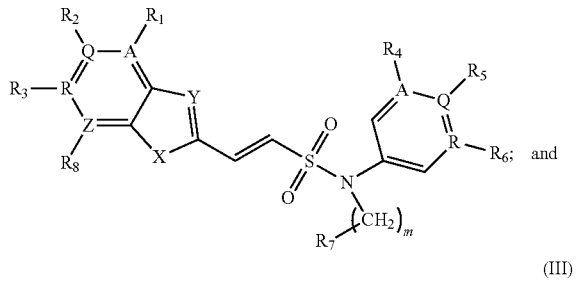

(II)

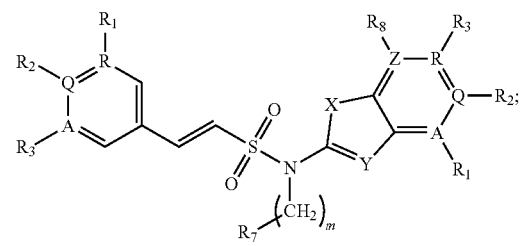

(III)

wherein:

m is an integer selected from the group consisting of 1 and 2;

A, Q, R, and Z are each independently selected from the group consisting of nitrogen and carbon, under the proviso that for compounds of formula (I), at least one of A, Q, or R is not carbon in at least one ring;

X is selected from the group consisting of $NH(CH_2)_n$, $S(CH_2)_n$, $O(CH_2)_n$, and $CR_9(CH_2)_n$, where n is an integer selected from the group consisting of 0, 1, 2, and 3;

Y is selected from the group consisting of N and CH;

$R_1$, $R_2$, $R_3$, $R_4$, $R_5$, $R_6$, $R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

$R_7$ is selected from the group consisting of:

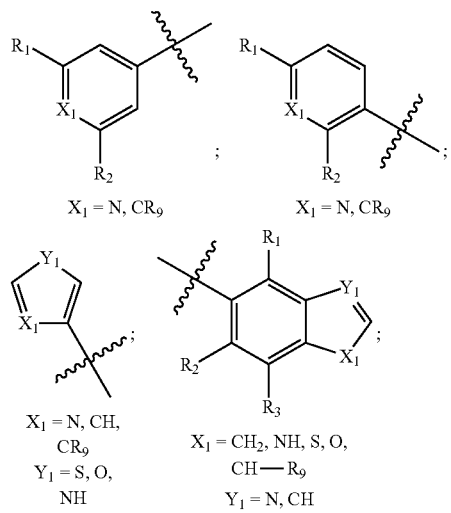

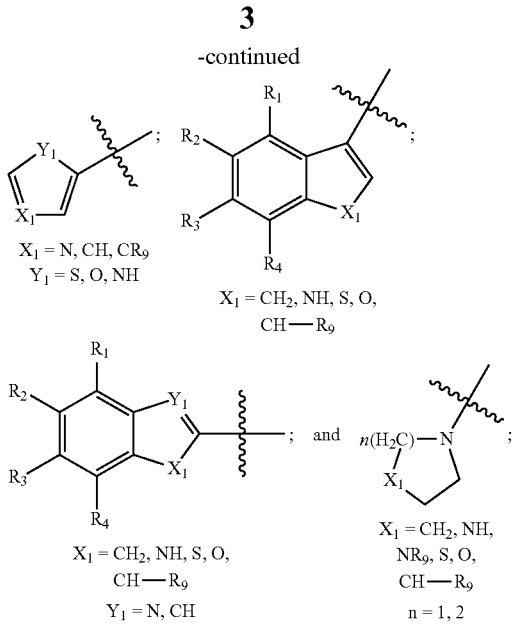

and a pharmaceutically acceptable salt, prodrug, or solvate thereof.

In other aspects, the presently disclosed subject matter provides a method for inhibiting a serine protease in a subject, the method comprising administering to the subject a compound of Formulae (I-III) in an amount effective to inhibit a serine protease. In certain aspects, the serine protease is chymase.

In yet other aspects, the presently disclosed subject matter provides a method for treating a serine protease-associated disease in a subject in need of treatment thereof, the method comprising administering to the subject a therapeutically-effective amount of a compound of Formulae (I-III). In some aspects, the serine protease-associated disease comprises a cardiovascular disease. In certain aspects, the serine-protease-associated disease is a chymase-associated disease. In yet other aspects, the compound of Formulae (I-III) is administered in combination with a second therapeutic agent.

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

BRIEF DESCRIPTION OF THE FIGURES

Figure 1:
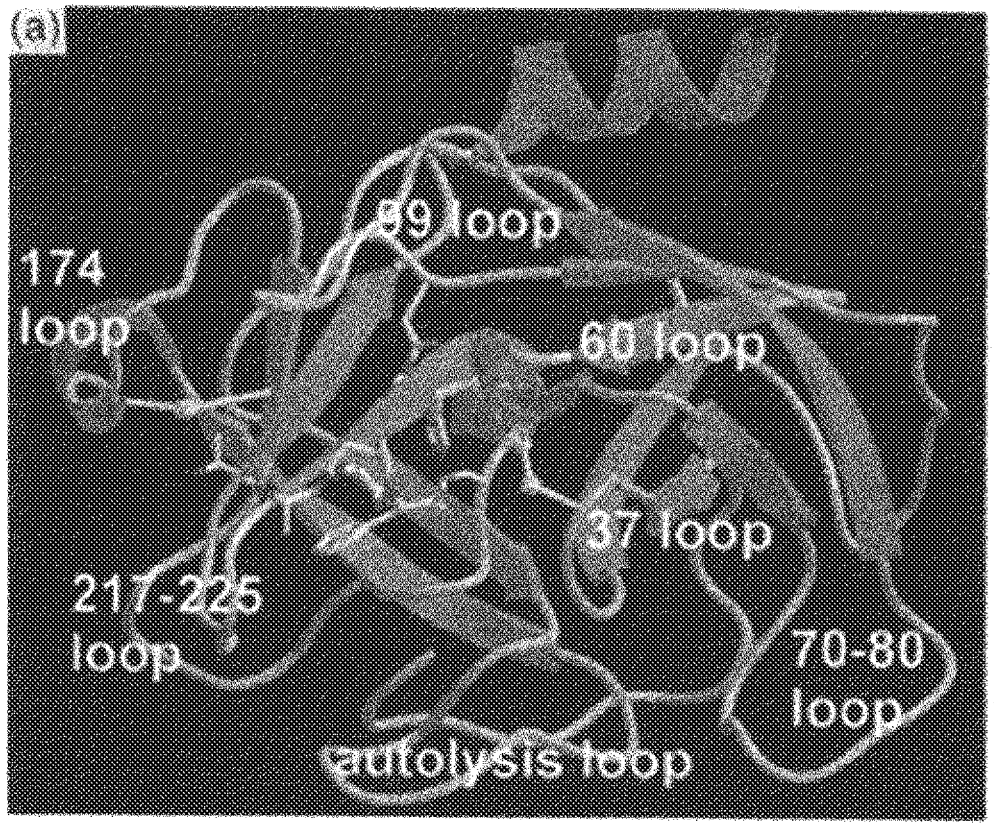
Figure 2:
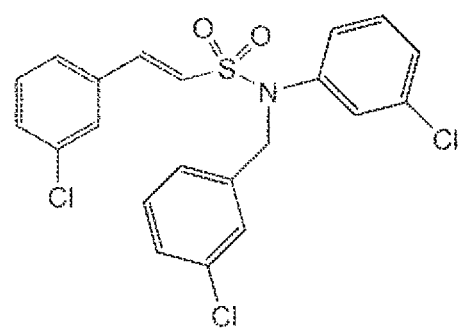
Figure 3:
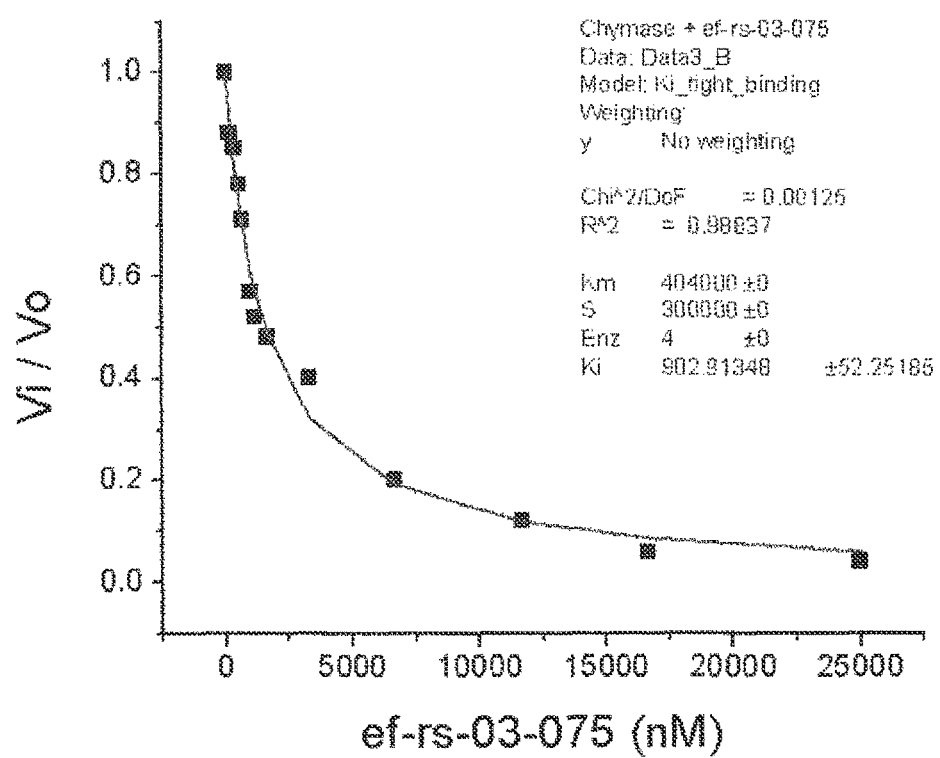

Having thus described the presently disclosed subject matter in general terms, reference will now be made to the accompanying Figures, which are not necessarily drawn to scale, and wherein:

FIG. 1 is a ribbon representation of the crystal structure of human chymase (prior art from Pereira et al, Journal of Molecular Biology, 286 (1), 163-173 (12 Feb. 1999));

FIG. 2 shows the chemical structure of a representative presently disclosed chymase inhibitor, ef-rs-03-075;

FIG. 3 demonstrates human chymase inhibition by ef-rs-03-075; and

Figure 4:
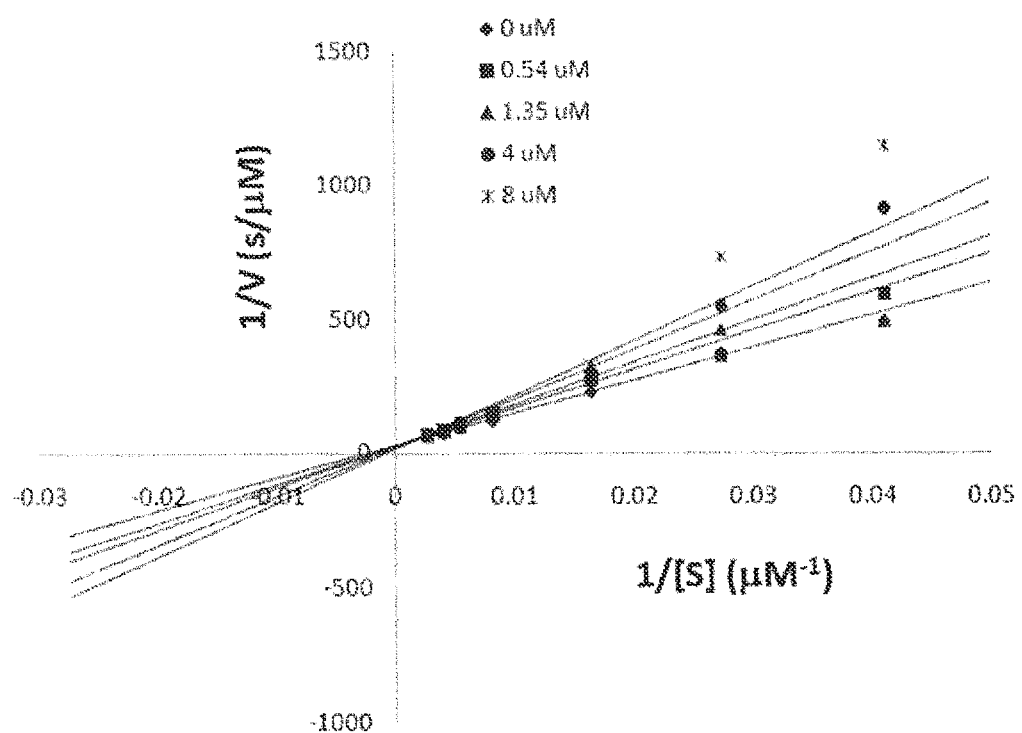

FIG. 4 shows a double reciprocal plot of substrate concentration vs. reaction velocity in the presence of various concentrations of ef-rs-03-075. Intersections on the y-axis of the fits of the data to the Michaelis-Menten equation indicate competitive inhibition of chymase by ef-rs-03-075.

DETAILED DESCRIPTION

The presently disclosed subject matter now will be described more fully hereinafter with reference to the accompanying Figures, in which some, but not all embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

I. High Affinity Serine Protease Inhibitors

The serine proteases are a group of proteolytic enzymes that have a common catalytic mechanism characterized by a particularly reactive serine (Ser) residue. Examples of serine proteases include, but are not limited to, chymase, trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa. See U.S. Pat. No. 7,928,137, which is incorporated herein by reference in its entirety.

Serine protease inhibitors play a central role in regulating a wide variety of physiological process, including coagulation, fibrinolysis, fertilization, development, malignancy, neuromuscular patterning, and inflammation. Serine protease inhibitors are thought to inhibit a variety of circulating proteases, as well as proteases that are activated or released in tissue. Such serine protease inhibitors inhibit critical cellular processes, such as adhesion, migration, free radical production and apoptosis. Further, animal experiments indicate that intravenously administered serine protease inhibitors, variants or cells expressing serine protease inhibitors, provide a protective effect against tissue damage.

Serine protease inhibitors also are thought to have potential beneficial uses in the treatment of disease in a wide variety of clinical areas including, but not limited to, oncology, neurology, haematology, pulmonary medicine, immunology, inflammation and infectious disease. In particular serine protease inhibitors may be beneficial in the treatment of thrombotic diseases, asthma, emphysema, cirrhosis, arthritis, carcinoma, melanoma, restenois, atheroma, trauma, shock and reperfusion injury.

More particularly, human chymase is a monomeric chymotrypsin-like serine protease stored in the secretory granules of mast cells. Human chymase is synthesized as a pre-pro-enzyme, which is converted to the pro-enzyme during translocation in the endoplasmic reticulum. In its active form within the secretory granules of mast cells, human chymase contains 226 amino acid residues and has a molecular weight of 25 kDa. Different crystallographic structures of human chymase have been deposited in a protein data bank, facilitating the structure-based optimization of chymase inhibitors.

Chymase is known to transform angiotensin I to angiotensin II and may contribute to activation of TGF-β, matrix proteases, and cytokines (Taipale et al., J. Biol. Chem., 1995, 270, 4689; Takai et al., Life ScL, 1996, 58, 591; Takai et al., Circulation, 1999, 100, 654). A potent and selective chymase inhibitor may have potential use as a treatment in various diseases including, but not limited to, chronic heart failure, atherosclerosis, restenosis, and myocardial infarction, by inhibiting local production of angiotensin II in the heart and release of TGF-β, two independent mediators of cardiac remodeling. A chymase inhibitor also might have potential use for treatment of mast cell mediated diseases, such as dermatitis, asthma, chronic obstructive pulmonary disease (COPD), and pulmonary inflammation, since chymase is implicated in microvascular leakage, neutrophil accumulation, the stimulation of mucus secretion, and the modulation of cytokines (He et al., Eur. J. Pharmacol., 1998, 352, 91).

Several small molecule chymase inhibitors have been reported to be efficacious in the cardiomyopathic hamster model of heart failure (Takai et al. J. Pharmacol. Exp. Ther. 2003, 305, 17), in carotid artery injury by a balloon catheter in dogs (Takai et al. J. Pharmacol. Exp. Ther, 2003, 304, 841), and in the hamster left anterior descending coronary artery ligation model of heart failure (WO 03/018061). Additionally, a chymase inhibitor has been demonstrated to be efficacious in a sheep asthma model (WO 2005/073214). See WO 2010/088195 A1 and WO 2010/019417 A2, each of which is incorporated herein in its entirety.

Chymase inhibitors comprising a benzimidazolone core structure are disclosed in H.Y. Lo et al., "Benzimidazolone as potent chymase inhibitor: Modulation of reactive metabolite formation in the hydrophobic ($P_1$) region," Bioorganic & Medicinal Chemistry Letters 21:4533-4539 (2011). Radiolabeled chymase inhibitors are disclosed in WO2009/102384 A2; small molecule chymase inhibitors are disclosed in WO2010/088195 A1 and WO2010/019417 A2; and chymase inhibitors for treating fibrosis are disclosed in U.S. Pat. No. 6,500,835 B2 to Fukami et al., each of which is incorporated herein by reference in their entirety.

A. Non-peptidic, Small Molecular Weight Competitive Serine Protease Inhibitors

In some embodiments, the presently disclosed subject matter provides non-peptidic, small molecular weight, competitive serine protease inhibitors having drug-like properties. More particularly, the presently disclosed subject matter provides a non-peptidic scaffold (e.g., an N-substituted diphenylethenesulfonamide) from which small molecular weight compounds capable of inhibiting serine proteases with high affinity in a competitive way can be synthesized. Because of the small size (e.g., mol. weight=452.78 g/mol (ef-rs-03-075)) and high affinity (e.g., 544 nM (ef-rs-03-075)) of the presently disclosed compounds, this scaffold facilitates lead optimization. The chemical structure of one representative compound, ef-rs-03-075, having this scaffold is shown in FIG. 2.

The presently disclosed scaffold provides the opportunity to synthesize various analogs by modification and/or addition and/or elimination of different chemical functionalities at different locations within the scaffold. Representative embodiments of such variations include, but are not limited to, compounds of Formulae (I-III):

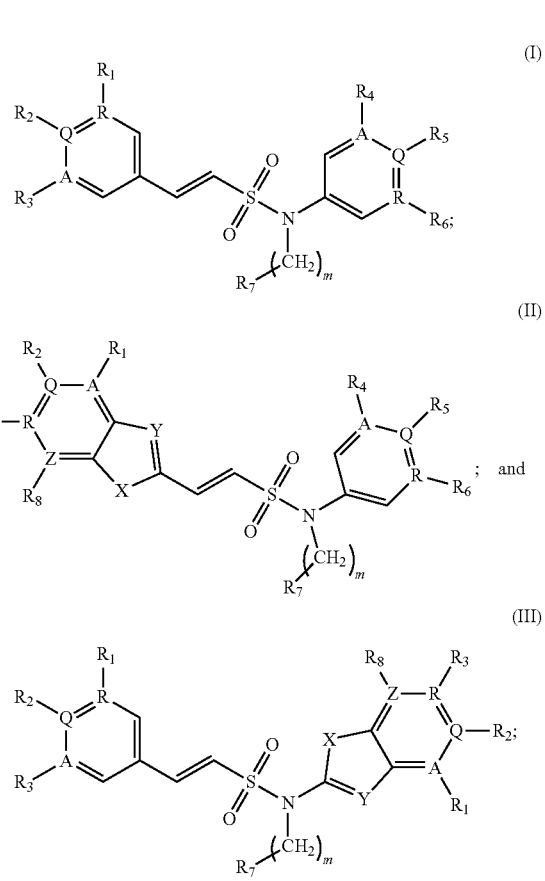

wherein:

m is an integer selected from the group consisting of 1 and 2;

A, Q, R, and Z are each independently selected from the group consisting of nitrogen and carbon, under the proviso that for compounds of formula (I), at least one of A, Q, or R is not carbon in at least one ring;

X is selected from the group consisting of $NH(CH_2)_n$, $S(CH_2)_n$, $O(CH_2)_n$, and $CR_9(CH_2)_n$, where n is an integer selected from the group consisting of 0, 1, 2, and 3;

Y is selected from the group consisting of N and CH;

$R_1$, $R_2$, $R_3$, $R_4$, $R_5$, $R_6$, $R_8$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

$R_7$ is selected from the group consisting of:

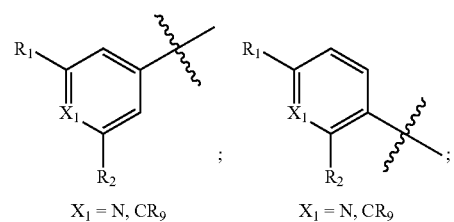

$X_1$ = N, $CR_9$     $X_1$ = N, $CR_9$

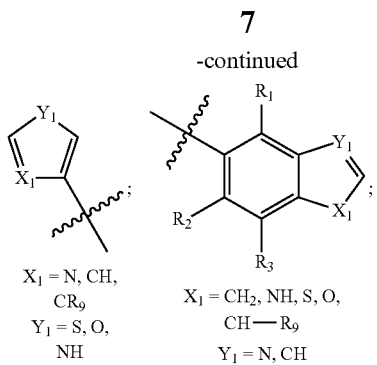

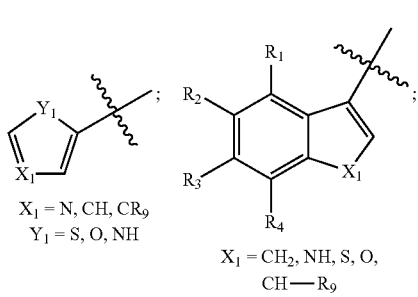

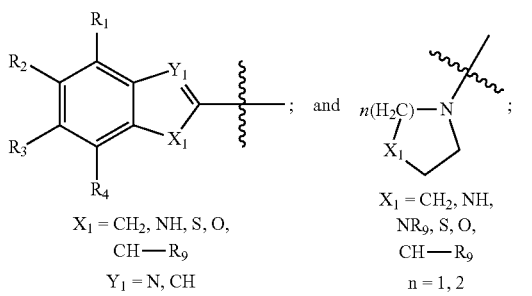

and a pharmaceutically acceptable salt, prodrug, or solvate thereof.

In particular embodiments, $R_1$-$R_6$ and $R_8$ are each independently selected from the group consisting of t-butyl, Cl, Br, methyl, —OCH$_3$, —NO$_2$, —NH$_2$, —OH, —CH$_2$OH, —CHO, —COOH, —COOCH$_3$, —COOCH$_2$CH$_3$, —CF$_3$, —CONHCH$_3$, —C≡N, —CONH$_2$, H, F, isopropyl, phenyl, cyclohexyl, benzyloxyl, and —SO$_3$H.

In yet more particular embodiments, the compound of Formula (I) is selected from the group consisting of:

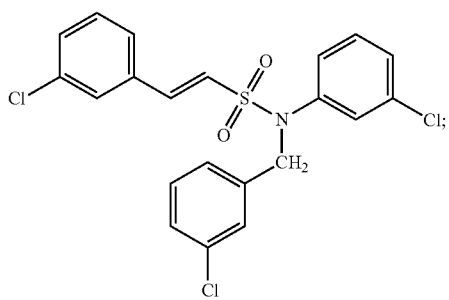

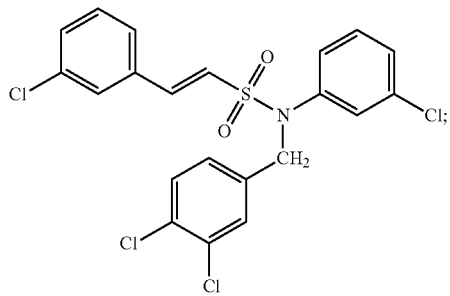

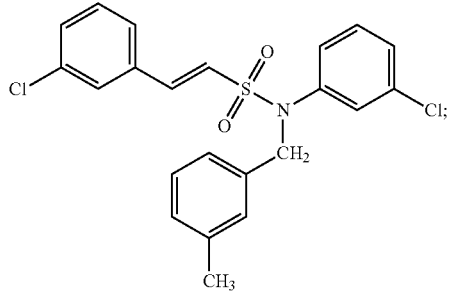

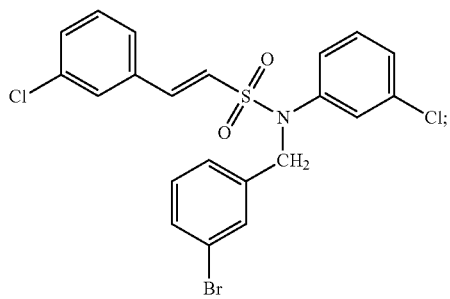

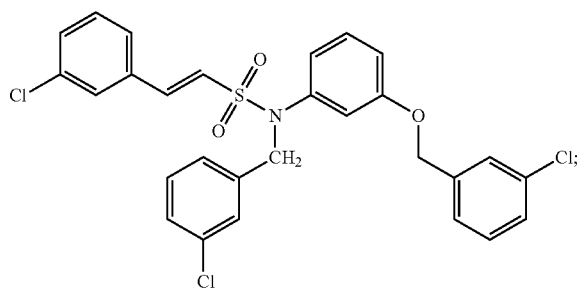

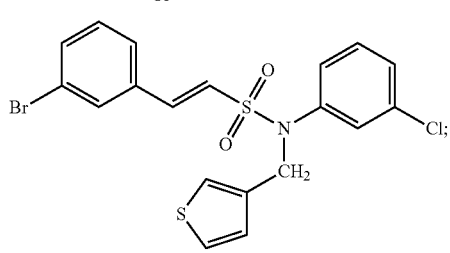

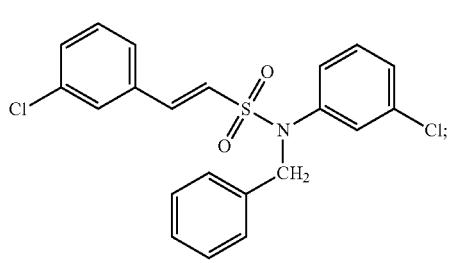

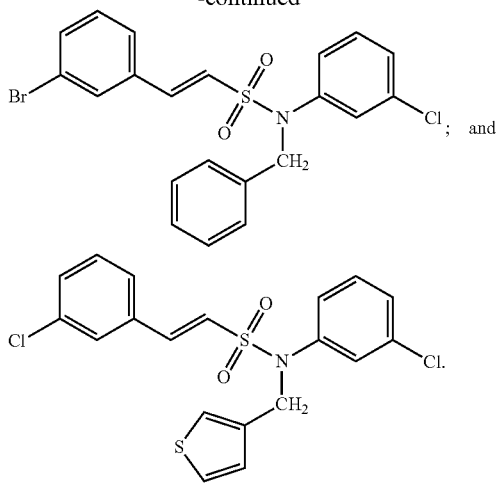

B. Method of Treating Serine Protease-Associated Diseases

Although the precise patho-physiological roles of chymase have yet to be determined, chymase has been implicated in microvascular leakage, neutrophil accumulation, the stimulation of mucus secretion, the modulation of cytokines, and the like. Chymase is a target for cardiovascular disease therapies (Doggrell et al., Can J Physiol Pharmacol. 2005 February; 83(2):123-30). In addition, chymase also has been proposed to play a critical role in diseases, such as rheumatoid arthritis (Kobayashi et al., Jpn J Pharmacol. 2002 September; 90(1):7-11), diabetic nephropathy (Huang et al., J Am Soc Nephrol. 2003 July; 14(7):1738-47), and inflammatory diseases (Muto et al., Idrugs., 2002, 12, 1141-50). See U.S. Pat. No. 7,575,888, which is incorporated herein by reference in its entirety.

A potent, chymase-selective inhibitor may be indicated in mast cell-mediated diseases, such as asthma, pulmonary inflammation, and chronic obstructive pulmonary diseases (COPD). Because chymase can play a role in the generation of cardiac and vascular wall angiotensin II, a chymase inhibitor may have potential use as an antihypertensive treatment for vascular wall injury and inflammation (atherosclerosis/restenosis), as well as cardiac hypertrophy.

Accordingly, in some embodiments, the presently disclosed subject matter provides a method of inhibiting a serine protease in a subject, the method comprising administering to the subject a compound of Formulae (I-III) as defined hereinabove in an amount effective to inhibit a serine protease.

As used herein, the term "inhibit," and grammatical derivations thereof, refers to the ability of a presently disclosed compound, e.g., a presently disclosed serine protease inhibitor of Formulae (I-III) to block, partially block, interfere, decrease, reduce or deactivate a serine protease. Thus, one of ordinary skill in the art would appreciate that the term "inhibit" encompasses a complete and/or partial loss of activity of a serine protease, e.g., a loss in activity by at least 10%, in some embodiments, a loss in activity by at least 20%, 30%, 50%, 75%, 95%, 98%, and up to and including 100%.

In yet further embodiments, the presently disclosed subject matter provides a method for treating a serine protease-associated disease in a subject in need of treatment thereof, the method comprising administering to the subject a therapeutically-effective amount of a compound of Formulae (I-III) as defined as hereinabove.

A "serine protease-associated disease" or a "serine protease-associated disorder" as used herein refers to a disease or disorder associated with over activity or over expression of a serine protease, or a disease or disorder that can be treated or ameliorated by decreasing the biological activity of a serine protease or by decreasing the amount of a serine protease in a subject, and subclinical manifestations or conditions that accompany with such a disease or disorder in the subject. In some embodiments, the serine protease-associated disease is a chymase-associated disease.

Exemplary "serine protease-associated diseases" include, but are not limited to asthma, including bronchial asthma, allergic rhinitis, fibrosis, hypertension, cardiac hypertrophy, heart failure, including congestive heart failure, rheumatoid arthritis, diabetic nephropathy, chronic obstructive pulmonary disease (COPD) and inflammatory diseases. See U.S. Pat. No. 7,892,779, which is incorporated herein by reference in its entirety.

The use of chymase inhibitors for treating fibrosis is disclosed in U.S. Pat. No. 6,500,835 B2, which is incorporated herein by reference in its entirety. As disclosed therein, fibrosis involving extracellular matrix dysbolism includes diseases whose onset is caused by the occurrence of extracellular matrix dysbolism, diseases whose conditions are aggravated by the occurrence of extracellular matrix dysbolism, and diseases whose cure is delayed by the occurrence of extracellular matrix dysbolism. Such diseases include, for example, scleroderma, pulmonary fibrosis, benign prostatomegaly, myocardial fibrogenesis following myocardial infarction, myocardial fibrosis, musculoskeletal fibrosis, post-surgical adhesion, hypertropic scars and keloids, cirrhosis, hepatic fibrosis, renal fibrosis, fibrous vascular disorders, and complications of diabetes such as retinitis due to fibrous microvasculitis, neurosis, nephropathy, and peripheral arteritis or a condition related to the same.

Other serine protease-associated diseases include, but are not limited to, urticaria (hives), atopic dermatitis, allergic conjunctivitis, mastocytosis, scleroderma, atherosclerosis (arteriosclerosis), myocardial ischemia, myocardial infarction, restenosis after percutaneous transluminal coronary angioplasty (PTCA), restenosis after bypass graft surgery, ischemic peripheral circulatory disorders, hyperaldosteronism, diabetic retinopathy, nephritis, glomerulosclerosis, renal insufficiency, psoriasis, solid tumor, postoperative adhesion, glaucoma, and ocular hypertension. See U.S. Pat. No. 7,888,348, which is incorporated herein by reference in its entirety. Yet other serine protease-associated diseases include hypercardia, diabetic or non-diabetic renal disease, ischemic re-perfusion disorder, keloid, psoriasis, solid tumors, and pulmonary hypertension. See U.S. Pat. No. 7,071,220, which is incorporated by reference in its entirety.

Further, since chymase is known to transform angiotensin I to angiotensin II and may contribute to activation of TGF-β, matrix proteases and cytokines, the inhibition of chymase is an approach for preventing and treating a variety of diseases or conditions. Examples, including those conditions and diseases disclosed hereinabove, include heart failure including chronic heart failure (non-ischemic), post-myocardial infarction heart failure (ischemic), acute myocardial infarction, reperfusion injury, left ventricular dysfunction, cardiac fibrosis, diastolic heart failure and hypertrophic cardiomyopathy, hypertension including pulmonary hypertension, systolic hypertension and resistant hypertension, including coronary artery disease, peripheral arterial occlusive disease, aneurism, stable/unstable angina, restenosis, diabetic nephropathy, atrial fibrillation/ventricular arrhythmias, valvular heart disease, pericardial diseases, renal insufficiency (chronic kidney disease, end stage renal disease), stroke. Chymase inhibitors also might be useful as a therapy involved with the following procedures: coronary artery bypass grafting, percutaneous coronary intervention and stenting.

Again, as also disclosed hereinabove, other diseases that could benefit from treatment with a chymase inhibitor, alone or in combination with a second therapeutic agent, include allergic rhinitis, dermatitis, asthma, chronic obstructive pulmonary disease (COPD), and pulmonary inflammation, asthma, osteoarthritis, bone resorption diseases, multiple sclerosis, Guillain-Barre syndrome, Crohn's disease, ulcerative colitis, psoriasis, graft versus host disease, systemic lupus erythematosus, rheumatoid arthritis, toxic shock syndrome, Alzheimer's disease, inflammatory bowel diseases, acute and chronic pain as well as symptoms of inflammation, thermal injury, adult respiratory distress syndrome (ARDS), multiple organ injury secondary to trauma, acute glomerulonephritis, dermatoses with acute inflammatory components, acute purulent meningitis or other central nervous system disorders, syndromes associated with hemodialysis, leukopherisis, granulocyte transfusion associated syndromes, and necrotizing entrerocolitis, traumatic arthritis, and sepsis. Reference in this regard may be made to U.S. Pat. Nos. 5,948,785; 6,271,238; 5,691,335; 5,814,631; 6,300,337; 6,323,219; U.S. Published Patent Application No. 2005-0245536 A1; EP 1,099,690; and Fukami, et al., Current Pharmaceutical Design 1998, vol. 4, pp. 439-453.

Further, chymase inhibitors may contribute to activation of cytokines and therefore may be useful for treating oncological diseases. Reference in this regard may be made to US 2005-0245536 A1. These diseases include, but are not limited to, solid tumors, such as cancers of the breast, respiratory tract, brain, reproductive organs, digestive tract, urinary tract, eye, liver, skin, head and neck, thyroid, parathyroid and their distant metastases. Those disorders also include lymphomas, sarcomas, and leukemias. Examples of breast cancer include, but are not limited to, invasive ductal carcinoma, invasive lobular carcinoma, ductal carcinoma in situ, and lobular carcinoma in situ. Examples of cancers of the respiratory tract include, but are not limited to small-cell and non-small-cell lung carcinoma, as well as bronchial adenoma and pleuropulmonary blastoma and mesothelioma. Examples of brain cancers include, but are not limited to brain stem, optic and hypophtalmic glioma, cerebella and cerebral astrocytoma, medulloblastoma, ependymoma, as well as pituitary, neuroectodermal and pineal tumor. Examples of peripheral nervous system tumors include, but are not limited to neuroblastoma, ganglioneuroblastoma, and peripheral nerve sheath tumors. Examples of tumors of the endocrine and exocrine system include, but are not limited to thyroid carcinoma, adrenocortical carcinoma, pheochromocytoma, and carcinoid tumors. Tumors of the male reproductive organs include, but are not limited to prostate and testicular cancer. Tumors of the female reproductive organs include, but are not limited to endometrial, cervical, ovarian, vaginal. See WO 2010/088195 A1 and WO 2010/019417 A2, each of which is incorporated herein in its entirety.

In particular embodiments, the presently disclosed subject matter provides a method for treating a cardiovascular disease, including cardiac and circulatory system diseases arising due to abnormal exacerbation of angiotensin II (Ang II) production, for example, cardiac insufficiency, hypercardia, stasis cardiac diseases, hypertension, arteriosclerosis, peripheral circulatory disorders, revasoconstriction after percutaneous transluminal coronary angioplasty (PCTA), diabetic renal disorders or non-diabetic renal disorders, coronary diseases including myocardial infarction, angioendothelia, or vascular disorders accompanying arterialization or atheroma. See U.S. Pat. No. 6,867,214, which is incorporated herein by reference in its entirety. In further embodiments, the presently disclosed method includes the repair of organs affected by stroke.

As used herein, the term "treating" can include reversing, alleviating, inhibiting the progression of, preventing or reducing the likelihood of the disease, disorder, or condition to which such term applies, or one or more symptoms or manifestations of such disease, disorder or condition. Preventing refers to causing a disease, disorder, condition, or symptom or manifestation of such, or worsening of the severity of such, not to occur. Accordingly, the presently disclosed serine protease inhibitors can be administered prophylactically to prevent or reduce the incidence or recurrence of the disease, disorder, or condition.

The "subject" treated by the presently disclosed methods in their many embodiments is desirably a human subject, although it is to be understood that the methods described herein are effective with respect to all vertebrate species, which are intended to be included in the term "subject." Accordingly, a "subject" can include a human subject for medical purposes, such as for the treatment of an existing condition or disease or the prophylactic treatment for preventing the onset of a condition or disease, or an animal subject for medical, veterinary purposes, or developmental purposes. Suitable animal subjects include mammals including, but not limited to, primates, e.g., humans, monkeys, apes, and the like; bovines, e.g., cattle, oxen, and the like; ovines, e.g., sheep and the like; caprines, e.g., goats and the like; porcines, e.g., pigs, hogs, and the like; equines, e.g., horses, donkeys, zebras, and the like; felines, including wild and domestic cats; canines, including dogs; lagomorphs, including rabbits, hares, and the like; and rodents, including mice, rats, and the like. An animal may be a transgenic animal. In some embodiments, the subject is a human including, but not limited to, fetal, neonatal, infant, juvenile, and adult subjects. Further, a "subject" can include a patient afflicted with or suspected of being afflicted with a condition or disease. Thus, the terms "subject" and "patient" are used interchangeably herein. The term "subject" also refers to an organism, tissue, cell, or collection of cells from a subject.

In general, the "effective amount" of an active agent or drug delivery device refers to the amount necessary to elicit the desired biological response. As will be appreciated by those of ordinary skill in this art, the effective amount of an agent or device may vary depending on such factors as the desired biological endpoint, the agent to be delivered, the makeup of the pharmaceutical composition, the target tissue, and the like.

The compounds of Formulae (I-III) described herein can be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies.

Accordingly, in further embodiments, depending upon the particular condition or disease state to be treated or prevented, additional therapeutic agents can be administered together with, i.e., in combination with, the presently disclosed inhibitors of Formulae (I-III). Such additional therapeutic agents can includes other agents for treating cardiovascular disease, include, but are not limited to, beta-blockers, ACE inhibitors, diuretics, nitrates, calcium channel blockers, and statins. Such additional agents may be administered separately, as part of a multiple dosage regimen, from the inhibitor-containing composition. Alternatively, these agents may be part of a single dosage form, mixed together with the presently disclosed inhibitor(s) in a single composition.

The term "combination" is used in its broadest sense and means that a subject is administered at least two agents, more particularly a compound of Formulae (I-III) and at least one additional therapeutic agent.

In some embodiments, the presently disclosed subject matter provides a method for treating a serine protease-associated disease in a subject in need of treatment thereof, the method comprising administering to the subject a therapeutically-effective amount of a compound of Formulae (I-III) in combination with an angiotensin I-converting enzyme (ACE) inhibitor. Any ACE inhibitor known in the art including, but not limited to, sulfhydryl-containing ACE inhibitors, such as captopril and zofenopril; dicarboxylate-containing ACE inhibitors, such as enalapril, ramipril, quinapril, perindopril, lisinopril, benazepril, imidapril, and zofenopril; phosphate-containing ACE inhibitors, such as fosinopril; naturally-occuring ACE inhibitors, such as, casokinins, lactokinins, and lactotripeptides, such as Val-Pro-Pro and Ile-Pro-Pro, and other ACE inhibitors, such as alacepril, cilazapril, delapril, imidapril, moexipril, rentiapril, spirapril, temocapril, and trandolapril, can be suitable for use with the presently disclosed methods. In particular embodiments, the combination therapy is used to treat a cardiovascular disease including, but not limited to, hypertension and heart failure. Typical dosages for ACE inhibitors include from about 1 mg to 50 mg per day, including 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50 mg per day, in some embodiments, from about 12.5 mg to about 37.5 mg per day, in some embodiments, from about 2.5 mg to about 30 mg per day, and in yet other embodiments, from about 5 mg to about 30 mg per day. It has been shown, for example, that combined chymase and ACE inhibition, relative to ACE inhibition alone, improved left ventricular (LV) function, decreased adverse cardiac remodeling, and improved survival after myocardial infarction (MI). See C.-C. Wei, et al., "Mast cell chymase limits the cardiac efficacy of Ang I-converting enzyme inhibitor therapy in rodents," J. Clin. Invest. 120(4):1229-1239 (2010).

In other embodiments, the method for treating a serine protease-associated disease includes administering to the subject in need of treatment a therapeutically-effective amount of a compound of Formulae (I-III) in combination with an alpha-blocker, also referred to as an alpha-adrenergic blocker. Representative alpha-blockers suitable for use with the presently disclosed methods include, but are not limited to, alfuzosin, doxazosin, prazosin, terazosin, and tamsulosin. Typical dosages for alpha blockers range from about 1 mg to about 20 mg per day, and, in some embodiments, 2 mg to 15 mg per day, and, in some embodiments, 1 mg to 5 mg per day. In some embodiments, the second therapeutic agent can be an alpha and a beta blocker, such as labetolol, for which a typical dosage is about 200 mg to about 800 mg per day.

In yet other embodiments, the method for treating a serine protease-associated disease includes administering to the subject in need of treatment a therapeutically-effective amount of a compound of Formulae (I-III) in combination with a central adrenergic inhibitor, also referred to as a central-acting agent, a central alpha agonist, or a central agonist. Representative central adrenergic inhibitors, along with typical dosages, include, but are not limited to, clonidine (about 0.1 mg to about 1 mg per day), guanabenz (about 4 mg to about 24 mg per day), guanfacine (about 1 mg to about 3 mg per day), and methyldopa (about 250 mg to about 1,000 mg per day).

In yet other embodiments, the method for treating a serine protease-associated disease includes administering to the subject in need of treatment a therapeutically-effective amount of a compound of Formulae (I-III) in combination with a beta blocker, also known as a beta-adrenergic blocker. Representative beta blockers include, but are not limited to, acebutolol, atenolol, bisoprolol, metoprolol, nadolol, nebivolol, pindolol, and propranolol. Typical dosages for beta blockers depend on the particular agent and can range from about 10 mg to about 600 mg per day.

In yet other embodiments, the method for treating a serine protease-associated disease includes administering to the subject in need of treatment a therapeutically-effective amount of a compound of Formulae (I-III) in combination with an angiotensin II receptor blocker. Representative angiotensin II receptor blockers include, but are not limited to, candesartan, eprosartan, irbesartan, losartan, olmesartan, telmisartan, and valsartan.

In yet other embodiments, the method for treating a serine protease-associated disease includes administering to the subject in need of treatment a therapeutically-effective amount of a compound of Formulae (I-III) in combination with a calcium channel blocker. Representative calcium channel blockers include, but are not limited to, amlodipine, diltiazem, felodipine, isradipine, nicardipine, nifedipine, nimodipine, nisoldipine, and verapamil. Typical dosages for calcium channel blockers depend on the particular agent and can range from about 30 mg to about 360 mg per day In yet other embodiments, the method for treating a serine protease-associated disease includes administering to the subject in need of treatment a therapeutically-effective amount of a compound of Formulae (I-III) in combination with a vasodilator. Representative vasodilators include, but are not limited to, hydralazine (about 50 mg to about 200 mg daily) and minoxidil (about 5 mg to about 20 mg per day). In some embodiments, the second therapeutic agent is a peripheral adrenergic antagonist, such as reserpine, which can be administered, e.g., about 0.1 mg to about 0.5 mg per day, alone or in combination with one or more other therapeutic agents.

In yet other embodiments, the method for treating a serine protease-associated disease includes administering to the subject in need of treatment a therapeutically-effective amount of a compound of Formulae (I-III) in combination with a phosphodiesterase (PDE) inhibitor. Representative PDE inhibitors include, but are not limited to, PDE1 inhibitors, such as vinpocetine; PDE2 inhibitors, such as erythro-9-(2-hydroxy-3-nonyl)adenine and anagrelide; PDE3 inhibitors, such as enoximone, milrinone, and levosimendon; PDE4 inhibitors, such as mesembrine, rolipram, ibudilast, piclamilast, luteolin, drotaverine, and roflumilast; PDE5 inhibitors, such as sildenafil, radalafil, vardenafil, udenafil, avanafil, dipyridamole, icariin, 4-methylpiperazine, and pyrazolopyrimidin-7-1; and non-selective phosphodiesterase inhibitors, including, but not limited to, caffeine, aminophylline, 3-isobutyl-1-methylxanthine, paraxanthine, pentoxifylline, theobromine, theophylline, and other methylated and non-methylated xanthines.

In yet other embodiments, the method for treating a serine protease-associated disease includes administering to the subject in need of treatment a therapeutically-effective amount of a compound of Formulae (I-III) in combination with a statin, also referred to as an HMG-CoA reductase inhibitor. Representative statins include, but are not limited to, atorvastatin, cerivastatin, fluvastatin, lovastatin, mevastatin, pitavastatin, pravastatin, rosuvastatin, simvastatin, and combinations therapies, such as simvastatin and ezetimibe, lovastatin and niacin (extended release), atorvastatin and amlodipine besylate, and simvastatin and niacin (extended release).

In yet other embodiments, the method for treating a serine protease-associated disease includes administering to the subject in need of treatment a therapeutically-effective amount of a compound of Formulae (I-III) in combination with a cholesterol-lowering agent. Representative cholesterol-lowering agents, along with typical dosage ranges, include, but are not limited to, cholestyramine, colestipol, gemfibrozil (about 600 mg twice daily), niacin (about 500 mg to about 1,000 mg three times a day), and probucol (about 500 mg twice daily).

In yet other embodiments, the method for treating a serine protease-associated disease includes administering to the subject in need of treatment a therapeutically-effective amount of a compound of Formulae (I-III) in combination with an antiarrhythmic agent. Representative antiarrhythmic agents include, but are not limited to, amiodarone, ibutilide, sotalol, dofetilide, and dronedarone. Typical dosages for such antiarrhythmic agents range from about 200 mg to about 600 mg per day. Other antiarrhythmic agents, along with typically dosages, include, but are not limited to, digoxin (about 0.125 mg to about 0.25 mg per day); disopyramide phosphate (about 100 mg three to four times a day); flecainide (about 100 mg to about 200 mg twice a day), propafenone (about 150 mg to about 300 mg three times a day), lidocaine (about 50 mg to about 100 mg per day via injection), mexiletine (about 150 to about 300 mg three to four times a day), procainamide (about 250 mg to about 750 mg every four hours (short acting) or about 500 mg to about 2,000 mg every six hours (sustained release), quinidine gluconate (about 200 mg to about 400 mg three to four times per day), and tocainide (about 200 mg to about 600 mg three times per day).

In yet other embodiments, the method for treating a serine protease-associated disease includes administering to the subject in need of treatment a therapeutically-effective amount of a compound of Formulae (I-III) in combination with a digitalis drug. Representative digitalis drugs, along with typical dosages, include, but are not limited to, digoxin (0.125 to about 0.25 mg per day) and digitoxin (about 0.05 to about 0.2 mg per day).

In yet other embodiments, the method for treating a serine protease-associated disease includes administering to the subject in need of treatment a therapeutically-effective amount of a compound of Formulae (I-III) in combination with a nitrate. Representative nitrates, along with typical dosages, include, but are not limited to, nitroglycerin (about 2.6 mg to about 27 mg per day oral tablets) and isosorbide dinitrate (about 5 mg to about 160 mg daily).

In yet other embodiments, the method for treating a serine protease-associated disease includes administering to the subject in need of treatment a therapeutically-effective amount of a compound of Formulae (I-III) in combination with an anticoagulant, antiplatelet, and/or thrombolytic agent. Representative anticoagulant, antiplatelet, and/or thrombolytic agents, along with typical dosages, include, but are not limited to, acetylsalicylic acid (about 81 mg to about 325 mg per day), dipyridamole (about 75 to about 400 mg per day), and warfarin (about 2.5 to about 7.5 mg per day for maintenance therapy).

In yet other embodiments, the method for treating a serine protease-associated disease includes administering to the subject in need of treatment a therapeutically-effective amount of a compound of Formulae (I-III) in combination with a diuretic. Representative diuretics, along with typical dosages, include, but are not limited to, chlorthalidone (about 12.5 mg to about 50 mg per day), hydrochlorothiazide (about 25 mg to about 50 mg per day), metolazone (about 2.5 mg to about 10 mg per day), bumetanide (about 0.5 mg to about 2.5 mg per day), furosemide (about 20 mg to about 40 mg per day), amiloride (about 5 mg to about 10 mg per day), spironolactone (about 25 mg to about 50 mg three to four times per day), and triamterene (about 50 mg to about 100 mg per day).

Other therapeutic agents suitable for use with the presently disclosed compounds of Formulae (I-III) include, but are not limited to, CETP inhibitors/apoA1 mimetics, adenosine diphosphate (P2Y12) inhibitors, aldosterone antagonists, factor Xa inhibitors, natriuretic peptides (ANP/BNP), renin inhibitors, Rho kinase inhibitors, Lipoprotein-associated phospholipase A2 inhibitors, cardiac glycosides, fibrates, Endothelin Receptor Antagonists, GPIIb/IIIa inhibitors, histone deacetylase inhibitors, nicotinic acid derivatives, vasopeptidase inhibitors, nitrites, fatty acid oxidation inhibitors, acyl-CoA:cholesterol acyltransferase inhibitors, microsomal triglyceride transfer protein inhibitors, thiazolidinediones, adenosine receptor modulators, cholesterol absorbtion inhibitors, Advanced Glycation End products/receptor (AGE/RAGE) interaction modulators/blockers, dipyridamole, gene therapy and cell therapy.

One of ordinary skill in the art also would appreciate that one or more of the second therapeutic agents alone or in combination can interact with one or more other therapeutic agents and that a therapy and/or dosage regimen should take this possibility into account.

The timing of administration of a compound of Formulae (I-III) and at least one additional therapeutic agent can be varied so long as the beneficial effects of the combination of these agents are achieved. Accordingly, the phrase "in combination with" refers to the administration of a compound of Formulae (I-III) and at least one additional therapeutic agent either simultaneously, sequentially, or a combination thereof. Therefore, a subject administered a combination of a compound of Formulae (I-III) and at least one additional therapeutic agent can receive compound of Formulae (I-III) and at least one additional therapeutic agent at the same time (i.e., simultaneously) or at different times (i.e., sequentially, in either order, on the same day or on different days), so long as the effect of the combination of both agents is achieved in the subject.

When administered sequentially, the agents can be administered within 1, 5, 10, 30, 60, 120, 180, 240 minutes or longer of one another. In other embodiments, agents administered sequentially, can be administered within 1, 5, 10, 15, 20 or more days of one another. Where the compound of Formulae (I-III) and at least one additional therapeutic agent are administered simultaneously, they can be administered to the subject as separate pharmaceutical compositions, each comprising either a compound of Formulae (I-III) or at least one additional therapeutic agent, or they can be administered to a subject as a single pharmaceutical composition comprising both agents.

When administered in combination, the effective concentration of each of the agents to elicit a particular biological response may be less than the effective concentration of each agent when administered alone, thereby allowing a reduction in the dose of one or more of the agents relative to the dose that would be needed if the agent was administered as a single agent. The effects of multiple agents may, but need not be, additive or synergistic. The agents may be administered multiple times.

In some embodiments, when administered in combination, the two or more agents can have a synergistic effect. As used herein, the terms "synergy," "synergistic," "synergistically" and derivations thereof, such as in a "synergistic effect" or a "synergistic combination" or a "synergistic composition" refer to circumstances under which the biological activity of a combination of a compound of Formulae (I-III) and at least one additional therapeutic agent is greater than the sum of the biological activities of the respective agents when administered individually.

Synergy can be expressed in terms of a "Synergy Index (SI)," which generally can be determined by the method described by F. C. Kull et al. Applied Microbiology 9, 538 (1961), from the ratio determined by:

$$Q_a Q_A + Q_b Q_B = \text{Synergy Index(SI)}$$

wherein:

$Q_A$ is the concentration of a component A, acting alone, which produced an end point in relation to component A;

$Q_a$ is the concentration of component A, in a mixture, which produced an end point;

$Q_B$ is the concentration of a component B, acting alone, which produced an end point in relation to component B; and $Q_b$ is the concentration of component B, in a mixture, which produced an end point.

Generally, when the sum of $Q_a/Q_A$ and $Q_b/Q_B$ is greater than one, antagonism is indicated. When the sum is equal to one, additivity is indicated. When the sum is less than one, synergism is demonstrated. The lower the SI, the greater the synergy shown by that particular mixture. Thus, a "synergistic combination" has an activity higher that what can be expected based on the observed activities of the individual components when used alone. Further, a "synergistically effective amount" of a component refers to the amount of the component necessary to elicit a synergistic effect in, for example, another therapeutic agent present in the composition.

C. Pharmaceutical Compositions and Administration

In another aspect, the presently disclosed subject matter provides a pharmaceutical composition including one or more compounds of Formulae (I-III) alone or in combination with one or more additional therapeutic agents in admixture with a pharmaceutically acceptable excipient. One of skill in the art will recognize that the pharmaceutical compositions include the pharmaceutically acceptable salts of the compounds described above.

Pharmaceutically acceptable salts are generally well known to those of ordinary skill in the art, and include salts of active compounds which are prepared with relatively non-toxic acids or bases, depending on the particular substituent moieties found on the compounds described herein. When compounds of the present disclosure contain relatively acidic functionalities, base addition salts can be obtained by contacting the neutral form of such compounds with a sufficient amount of the desired base, either neat or in a suitable inert solvent.

Examples of pharmaceutically acceptable base addition salts include sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like {see, for example, Berge et al, "Pharmaceutical Salts", Journal of Pharmaceutical Science, 1977, 66, 1-19). Certain specific compounds of the present disclosure contain both basic and acidic functionalities that allow the compounds to be converted into either base or acid addition salts.

Accordingly, pharmaceutically acceptable salts suitable for use with the presently disclosed subject matter include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000).

In therapeutic and/or diagnostic applications, the compounds of the disclosure can be formulated for a variety of modes of administration, including systemic and topical or localized administration. Techniques and formulations generally may be found in Remington: The Science and Practice of Pharmacy ($20^{th}$ ed.) Lippincott, Williams & Wilkins (2000). Depending on the specific conditions being treated, such agents may be formulated into liquid or solid dosage forms and administered systemically or locally. The agents may be delivered, for example, in a timed- or sustained-slow release form as is known to those skilled in the art. Techniques for formulation and administration may be found in Remington: The Science and Practice of Pharmacy ($20^{th}$ ed.) Lippincott, Williams & Wilkins (2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articullar, intra-sternal, intrasynovial, intra-hepatic, intralesional, intracranial, intraperitoneal, intranasal, or intraocular injections or other modes of delivery.

For injection, the agents of the disclosure may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, the compositions of the present disclosure, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a subject (e.g., patient) to be treated.

For nasal or inhalation delivery, the agents of the disclosure also may be formulated by methods known to those of skill in the art, and may include, for example, but not limited to, examples of solubilizing, diluting, or dispersing substances, such as saline; preservatives, such as benzyl alcohol; absorption promoters; and fluorocarbons.

Pharmaceutical compositions suitable for use in the present disclosure include compositions wherein the active ingredients are contained in an effective amount to achieve its intended purpose. Determination of the effective amounts is well within the capability of those skilled in the art, especially in light of the detailed disclosure provided herein. Generally, the compounds according to the disclosure are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. A non-limiting dosage is 10 to 30 mg per day. The exact dosage will depend upon the route of administration, the form in which the compound is administered, the subject to be treated, the body weight of the subject to be treated, and the preference and experience of the attending physician.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

D. Definitions

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

While the following terms in relation to compounds of Formulae (I-III) are believed to be well understood by one of ordinary skill in the art, the following definitions are set forth to facilitate explanation of the presently disclosed subject matter. These definitions are intended to supplement and illustrate, not preclude, the definitions that would be apparent to one of ordinary skill in the art upon review of the present disclosure.

The terms substituted, whether preceded by the term "optionally" or not, and substituent, as used herein, refer to the ability, as appreciated by one skilled in this art, to change one functional group for another functional group on a molecule, provided that the valency of all atoms is maintained. When more than one position in any given structure may be substituted with more than one substituent selected from a specified group, the substituent may be either the same or different at every position. The substituents also may be further substituted (e.g., an aryl group substituent may have another substituent off it, such as another aryl group, which is further substituted at one or more positions).

Where substituent groups or linking groups are specified by their conventional chemical formulae, written from left to right, they equally encompass the chemically identical substituents that would result from writing the structure from right to left, e.g., —CH$_2$O— is equivalent to —OCH$_2$—; —C(=O)O— is equivalent to —OC(=O)—; —OC(=O)NR— is equivalent to —NRC(=O)O—, and the like.

When the term "independently selected" is used, the substituents being referred to (e.g., R groups, such as groups R$_1$, R$_2$, and the like, or variables, such as "m" and "n"), can be identical or different. For example, both R$_1$ and R$_2$ can be substituted alkyls, or R$_1$ can be hydrogen and R$_2$ can be a substituted alkyl, and the like.

The terms "a," "an," or "a(n)," when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

A named "R" or group will generally have the structure that is recognized in the art as corresponding to a group having that name, unless specified otherwise herein. For the purposes of illustration, certain representative "R" groups as set forth above are defined below.

Descriptions of compounds of the present disclosure are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

Unless otherwise explicitly defined, a "substituent group," as used herein, includes a functional group selected from one or more of the following moieties, which are defined herein:

The term hydrocarbon, as used herein, refers to any chemical group comprising hydrogen and carbon. The hydrocarbon may be substituted or unsubstituted. As would be known to one skilled in this art, all valencies must be satisfied in making any substitutions. The hydrocarbon may be unsaturated, saturated, branched, unbranched, cyclic, polycyclic, or heterocyclic. Illustrative hydrocarbons are further defined herein below and include, for example, methyl, ethyl, n-propyl, isopropyl, cyclopropyl, allyl, vinyl, n-butyl, tert-butyl, ethynyl, cyclohexyl, methoxyl, diethylamino, and the like.

The term "alkyl," by itself or as part of another substituent, means, unless otherwise stated, a straight (i.e., unbranched) or branched chain, acyclic or cyclic hydrocarbon group, or combination thereof, which may be fully saturated, mono- or polyunsaturated and can include di- and multivalent groups, having the number of carbon atoms designated (i.e., $C_1$-$C_{10}$ means one to ten carbons, including 1, 2, 3, 4, 5, 6, 7, 8, 9, and 10 carbons). In particular embodiments, the term "alkyl" refers to $C_{1-20}$ inclusive, including 1, 2, 3, 4, 5, 6, 7, 8, 9, 10, 11, 12, 13, 14, 15, 16, 17, 18, 19, and 20 carbons, linear (i.e., "straight-chain"), branched, or cyclic, saturated or at least partially and in some cases fully unsaturated (i.e., alkenyl and alkynyl) hydrocarbon radicals derived from a hydrocarbon moiety containing between one and twenty carbon atoms by removal of a single hydrogen atom.

Representative saturated hydrocarbon groups include, but are not limited to, methyl, ethyl, n-propyl, isopropyl, n-butyl, isobutyl, sec-butyl, tert-butyl, n-pentyl, sec-pentyl, iso-pentyl, neopentyl, n-hexyl, sec-hexyl, n-heptyl, n-octyl, n-decyl, n-undecyl, dodecyl, cyclohexyl, (cyclohexyl)methyl, cyclopropylmethyl, and homologs and isomers thereof.

"Branched" refers to an alkyl group in which a lower alkyl group, such as methyl, ethyl or propyl, is attached to a linear alkyl chain. "Lower alkyl" refers to an alkyl group having 1 to about 8 carbon atoms (i.e., a $C_{1-8}$ alkyl), e.g., 1, 2, 3, 4, 5, 6, 7, or 8 carbon atoms. "Higher alkyl" refers to an alkyl group having about 10 to about 20 carbon atoms, e.g., 10, 11, 12, 13, 14, 15, 16, 17, 18, 19, or 20 carbon atoms. In certain embodiments, "alkyl" refers, in particular, to $C_{1-8}$ straight-chain alkyls. In other embodiments, "alkyl" refers, in particular, to $C_{1-8}$ branched-chain alkyls.

Alkyl groups can optionally be substituted (a "substituted alkyl") with one or more alkyl group substituents, which can be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There can be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "heteroalkyl," by itself or in combination with another term, means, unless otherwise stated, a stable straight or branched chain, or cyclic hydrocarbon group, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$5—S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

As described above, heteroalkyl groups, as used herein, include those groups that are attached to the remainder of the molecule through a heteroatom, such as —C(O)R', —C(O)NR', —NR'R", —OR', —SR, —S(O)R, and/or —S(O$_2$)R'. Where "heteroalkyl" is recited, followed by recitations of specific heteroalkyl groups, such as —NR'R or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

"Cyclic" and "cycloalkyl" refer to a non-aromatic mono- or multicyclic ring system of about 3 to about 10 carbon atoms, e.g., 3, 4, 5, 6, 7, 8, 9, or 10 carbon atoms. The cycloalkyl group can be optionally partially unsaturated. The cycloalkyl group also can be optionally substituted with an alkyl group substituent as defined herein, oxo, and/or alkylene. There can be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl, and fused ring systems, such as dihydro- and tetrahydronaphthalene, and the like.

The term "cycloalkylalkyl," as used herein, refers to a cycloalkyl group as defined hereinabove, which is attached to the parent molecular moiety through an alkyl group, also as defined above. Examples of cycloalkylalkyl groups include cyclopropylmethyl and cyclopentylethyl.

The terms "cycloheteroalkyl" or "heterocycloalkyl" refer to a non-aromatic ring system, unsaturated or partially unsaturated ring system, such as a 3- to 10-member substituted or unsubstituted cycloalkyl ring system, including one or more heteroatoms, which can be the same or different, and are selected from the group consisting of nitrogen (N), oxygen (O), sulfur (S), phosphorus (P), and silicon (Si), and optionally can include one or more double bonds.

The cycloheteroalkyl ring can be optionally fused to or otherwise attached to other cycloheteroalkyl rings and/or non-aromatic hydrocarbon rings. Heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocylic refers to a non-aromatic 5-, 6-, or 7-membered ring or a polycyclic group wherein at least one ring atom is a heteroatom selected from O, S, and N (wherein the nitrogen and sulfur heteroatoms may be optionally oxidized), including, but not limited to, a bi- or tri-cyclic group, comprising fused six-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Representative cycloheteroalkyl ring systems include, but are not limited to pyrrolidinyl, pyrrolinyl, imidazolidinyl, imidazolinyl, pyrazolidinyl, pyrazolinyl, piperidyl, piperazinyl, indolinyl, quinuclidinyl, morpholinyl, thiomorpholinyl, thiadiazinanyl, tetrahydrofuranyl, and the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl."

More particularly, the term "alkenyl" as used herein refers to a monovalent group derived from a $C_{1-20}$ inclusive straight or branched hydrocarbon moiety having at least one carbon-carbon double bond by the removal of a single hydrogen atom. Alkenyl groups include, for example, ethenyl (i.e., vinyl), propenyl, butenyl, 1-methyl-2-buten-1-yl, pentenyl, hexenyl, octenyl, and butadienyl.

The term "cycloalkenyl" as used herein refers to a cyclic hydrocarbon containing at least one carbon-carbon double bond. Examples of cycloalkenyl groups include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "alkynyl" as used herein refers to a monovalent group derived from a straight or branched $C_{1-20}$ hydrocarbon of a designed number of carbon atoms containing at least one carbon-carbon triple bond. Examples of "alkynyl" include ethynyl, 2-propynyl (propargyl), 1-propynyl, pentynyl, hexynyl, heptynyl, and allenyl groups, and the like.

The term "alkylene" by itself or a part of another substituent refers to a straight or branched bivalent aliphatic hydrocarbon group derived from an alkyl group having from 1 to about 20 carbon atoms, e.g., 1, 2, 3, 4, 5, 6, 7, 8, 9, 10, 11, 12, 13, 14, 15, 16, 17, 18, 19, or 20 carbon atoms. The alkylene group can be straight, branched or cyclic. The alkylene group also can be optionally unsaturated and/or substituted with one or more "alkyl group substituents." There can be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—$CH_2$—); ethylene (—$CH_2$—$CH_2$—); propylene (—$(CH_2)_3$—); cyclohexylene (—$C_6H_{10}$—); —CH═CH—CH═CH—; —CH═CH—$CH_2$—; —$CH_2CH_2CH_2CH_2$—, —$CH_2CH$═$CHCH_2$—, —$CH_2CsCCH_2$—, —$CH_2CH_2CH(CH_2CH_2CH_3)CH_2$—, —$(CH_2)_q$—N(R)—$(CH_2)_r$—, wherein each of q and r is independently an integer from 0 to about 20, e.g., 0, 1, 2, 3, 4, 5, 6, 7, 8, 9, 10, 11, 12, 13, 14, 15, 16, 17, 18, 19, or 20, and R is hydrogen or lower alkyl; methylenedioxyl (—O—$CH_2$—O—); and ethylenedioxyl (—O—$(CH_2)_2$—O—). An alkylene group can have about 2 to about 3 carbon atoms and can further have 6-20 carbons. Typically, an alkyl (or alkylene) group will have from 1 to 24 carbon atoms, with those groups having 10 or fewer carbon atoms being some embodiments of the present disclosure. A "lower alkyl" or "lower alkylene" is a shorter chain alkyl or alkylene group, generally having eight or fewer carbon atoms.

The term "heteroalkylene" by itself or as part of another substituent means a divalent group derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O)OR'— and —R'OC(O)—.

The term "aryl" means, unless otherwise stated, an aromatic hydrocarbon substituent that can be a single ring or multiple rings (such as from 1 to 3 rings), which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent forms of aryl and heteroaryl, respectively.

For brevity, the term "aryl" when used in combination with other terms (e.g., aryloxo, arylthioxo, aryalkyl) includes both aryl and heteroaryl rings as defined above. Thus, the terms "arylalkyl" and "heteroarylalkyl" are meant to include those groups in which an aryl or heteroaryl group is attached to an alkyl group (e.g., benzyl, phenethyl, pyridylmethyl, furylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxyl)propyl, and the like). However, the term "haloaryl," as used herein is meant to cover only aryls substituted with one or more halogens.

Where a heteroalkyl, heterocycloalkyl, or heteroaryl includes a specific number of members (e.g. "3 to 7 membered"), the term "member" refers to a carbon or heteroatom.

Further, a structure represented generally by the formula:

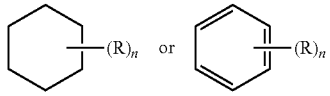

as used herein refers to a ring structure, for example, but not limited to a 3-carbon, a 4-carbon, a 5-carbon, a 6-carbon, a 7-carbon, and the like, aliphatic and/or aromatic cyclic compound, including a saturated ring structure, a partially saturated ring structure, and an unsaturated ring structure, comprising a substituent R group, wherein the R group can be present or absent, and when present, one or more R groups can each be substituted on one or more available carbon atoms of the ring structure. The presence or absence of the R group and number of R groups is determined by the value of the variable "n," which is an integer generally having a value ranging from 0 to the number of carbon atoms on the ring available for substitution. Each R group, if more than one, is substituted on an available carbon of the ring structure rather than on another R group. For example, the structure above where n is 0 to 2 would comprise compound groups including, but not limited to:

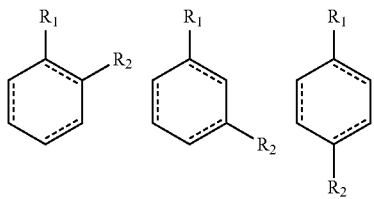

and the like.

A dashed line representing a bond in a cyclic ring structure indicates that the bond can be either present or absent in the ring. That is, a dashed line representing a bond in a cyclic ring structure indicates that the ring structure is selected from the group consisting of a saturated ring structure, a partially saturated ring structure, and an unsaturated ring structure.

The symbol ( ⌇⌇⌇ ) denotes the point of attachment of a moiety to the remainder of the molecule.

When a named atom of an aromatic ring or a heterocyclic aromatic ring is defined as being "absent," the named atom is replaced by a direct bond.

Each of above terms (e.g., "alkyl," "heteroalkyl," "cycloalkyl, and "heterocycloalkyl", "aryl," "heteroaryl," "phosphonate," and "sulfonate" as well as their divalent derivatives) are meant to include both substituted and unsubstituted forms of the indicated group. Optional substituents for each type of group are provided below.

Substituents for alkyl, heteroalkyl, cycloalkyl, heterocycloalkyl monovalent and divalent derivative groups (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such groups. R', R", R''' and R'''' each may independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. As used herein, an "alkoxy" group is an alkyl attached to the remainder of the molecule through a divalent oxygen. When a compound of the disclosure includes more than one R group, for example, each of the R groups is independently selected as are each R', R", R''' and R'''' groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for alkyl groups above, exemplary substituents for aryl and heteroaryl groups (as well as their divalent derivatives) are varied and are selected from, for example: halogen, —OR', —NR'R", —SR', —SiR'R"R''', —OC(O)R', —C(O)R', —CO$_2$R', —C(O)NR'R", —OC(O)NR'R", —NR"C(O)R', —NR'—C(O)NR"R''', —NR"C(O)OR', —NR—C(NR'R"R''')=NR'''', —NR—C(NR'R")=NR'''—S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxo, and fluoro(C$_1$-C$_4$)alkyl, in a number ranging from zero to the total number of open valences on aromatic ring system; and where R', R", R''' and R'''' may be independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the disclosure includes more than one R group, for example, each of the R groups is independently selected as are each R', R", R''' and R'''' groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4.

One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R''')$_d$—, where s and d are independently integers of from 0 to 3, and X' is —O—, —NR'—, —S—, —S(O)—, —S(O)$_2$—, or —S(O)$_2$NR'—. The substituents R, R', R" and R'" may be independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "acyl" refers to an organic acid group wherein the —OH of the carboxyl group has been replaced with another substituent and has the general formula RC(=O)—, wherein R is an alkyl, alkenyl, alkynyl, aryl, carbocylic, heterocyclic, or aromatic heterocyclic group as defined herein). As such, the term "acyl" specifically includes arylacyl groups, such as an acetylfuran and a phenacyl group. Specific examples of acyl groups include acetyl and benzoyl. Acyl groups also are intended to include amides, —RC(=O) NR', esters, —RC(=O)OR', ketones, —RC(=O)R', and aldehydes, —RC(=O)H.

The terms "alkoxyl" or "alkoxy" are used interchangeably herein and refer to a saturated (i.e., alkyl-O—) or unsaturated (i.e., alkenyl-O— and alkynyl-O—) group attached to the parent molecular moiety through an oxygen atom, wherein the terms "alkyl," "alkenyl," and "alkynyl" are as previously described and can include $C_{1-20}$ inclusive, linear, branched, or cyclic, saturated or unsaturated oxo-hydrocarbon chains, including, for example, methoxyl, ethoxyl, propoxyl, isopropoxyl, n-butoxyl, sec-butoxyl, t-butoxyl, and n-pentoxyl, neopentoxyl, n-hexoxyl, and the like.

The term "alkoxyalkyl" as used herein refers to an alkyl-O-alkyl ether, for example, a methoxyethyl or an ethoxymethyl group.

"Aryloxyl" refers to an aryl-O— group wherein the aryl group is as previously described, including a substituted aryl. The term "aryloxyl" as used herein can refer to phenyloxyl or hexyloxyl, and alkyl, substituted alkyl, halo, or alkoxyl substituted phenyloxyl or hexyloxyl.

"Aralkyl" refers to an aryl-alkyl-group wherein aryl and alkyl are as previously described, and included substituted aryl and substituted alkyl. Exemplary aralkyl groups include benzyl, phenylethyl, and naphthylmethyl.

"Aralkyloxyl" refers to an aralkyl-O— group wherein the aralkyl group is as previously described. An exemplary aralkyloxyl group is benzyloxyl, i.e., $C_6H_5$—$CH_2$—O—. An aralkyloxyl group can optionally be substituted.

"Alkoxycarbonyl" refers to an alkyl-O—C(=O)— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—C(=O)— group. Exemplary aryloxycarbonyl groups include phenoxy- and naphthoxy-carbonyl.

"Aralkoxycarbonyl" refers to an aralkyl-O—C(=O)— group. An exemplary aralkoxycarbonyl group is benzyloxycarbonyl.

"Carbamoyl" refers to an amide group of the formula —C(=O)NH$_2$. "Alkylcarbamoyl" refers to a R'RN—C (=O)— group wherein one of R and R' is hydrogen and the other of R and R' is alkyl and/or substituted alkyl as previously described. "Dialkylcarbamoyl" refers to a R'RN—C (=O)— group wherein each of R and R' is independently alkyl and/or substituted alkyl as previously described.

The term carbonyldioxyl, as used herein, refers to a carbonate group of the formula —O—C(=O)—OR.

"Acyloxyl" refers to an acyl-O— group wherein acyl is as previously described.

The term "amino" refers to the —NH$_2$ group and also refers to a nitrogen containing group as is known in the art derived from ammonia by the replacement of one or more hydrogen radicals by organic radicals. For example, the terms "acylamino" and "alkylamino" refer to specific N-substituted organic radicals with acyl and alkyl substituent groups respectively.

An "aminoalkyl" as used herein refers to an amino group covalently bound to an alkylene linker. More particularly, the terms alkylamino, dialkylamino, and trialkylamino as used herein refer to one, two, or three, respectively, alkyl groups, as previously defined, attached to the parent molecular moiety through a nitrogen atom. The term alkylamino refers to a group having the structure —NHR' wherein R' is an alkyl group, as previously defined; whereas the term dialkylamino refers to a group having the structure —NR'R", wherein R' and R" are each independently selected from the group consisting of alkyl groups. The term trialkylamino refers to a group having the structure —NR'R"R'", wherein R', R", and R'" are each independently selected from the group consisting of alkyl groups. Additionally, R', R", and/or R'" taken together may optionally be —(CH$_2$)$_k$— where k is an integer from 2 to 6. Examples include, but are not limited to, methylamino, dimethylamino, ethylamino, diethylamino, diethylaminocarbonyl, methylethylamino, iso-propylamino, piperidino, trimethylamino, and propylamino The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

The terms alkylthioether and thioalkoxyl refer to a saturated (i.e., alkyl-S—) or unsaturated (i.e., alkenyl-S— and alkynyl-S—) group attached to the parent molecular moiety through a sulfur atom. Examples of thioalkoxyl moieties include, but are not limited to, methylthio, ethylthio, propylthio, isopropylthio, n-butylthio, and the like.

"Acylamino" refers to an acyl-NH— group wherein acyl is as previously described. "Aroylamino" refers to an aroyl-NH— group wherein aroyl is as previously described.

The term "carbonyl" refers to the —C(=O)— group, and can include an aldehyde group represented by the general formula R—C(=O)H.

The term "carboxyl" refers to the —COOH group. Such groups also are referred to herein as a "carboxylic acid" moiety.

The terms "halo," "halide," or "halogen" as used herein refer to fluoro, chloro, bromo, and iodo groups. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "hydroxyl" refers to the —OH group.

The term "hydroxyalkyl" refers to an alkyl group substituted with an —OH group.

The term "mercapto" refers to the —SH group.

The term "oxo" as used herein means an oxygen atom that is double bonded to a carbon atom or to another element.

The term "nitro" refers to the —NO$_2$ group.

The term "thio" refers to a compound described previously herein wherein a carbon or oxygen atom is replaced by a sulfur atom.

The term "sulfate" refers to the —SO$_4$ group.

The term thiohydroxyl or thiol, as used herein, refers to a group of the formula —SH.

More particularly, the term "sulfide" refers to compound having a group of the formula —SR.

The term "sulfone" refers to compound having a sulfonyl group —S(O$_2$)R.

The term "sulfoxide" refers to a compound having a sulfinyl group —S(O)R

The term ureido refers to a urea group of the formula —NH—CO—NH$_2$.

Throughout the specification and claims, a given chemical formula or name shall encompass all tautomers, congeners, and optical- and stereoisomers, as well as racemic mixtures where such isomers and mixtures exist.

Certain compounds of the present disclosure may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those which are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefenic bonds or other centers of geometric asymmetry, and unless specified otherwise, it is intended that the compounds include both E and Z geometric isomers. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure.

It will be apparent to one skilled in the art that certain compounds of this disclosure may exist in tautomeric forms, all such tautomeric forms of the compounds being within the scope of the disclosure. The term "tautomer," as used herein, refers to one of two or more structural isomers which exist in equilibrium and which are readily converted from one isomeric form to another.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this disclosure.

The compounds of the present disclosure may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are encompassed within the scope of the present disclosure.

The compounds of the present disclosure may exist as salts. The present disclosure includes such salts. Examples of applicable salt forms include hydrochlorides, hydrobromides, sulfates, methanesulfonates, nitrates, maleates, acetates, citrates, fumarates, tartrates (e.g. (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present disclosure contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

In addition to salt forms, the present disclosure provides compounds, which are in a prodrug form. Prodrugs of the compounds described herein are those compounds that readily undergo chemical changes under physiological conditions to provide the compounds of the present disclosure. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter. The synthetic descriptions and specific examples that follow are only intended for the purposes of illustration, and are not to be construed as limiting in any manner to make compounds of the disclosure by other methods.

Example 1

Chemical Synthesis of ef-rs-03-075

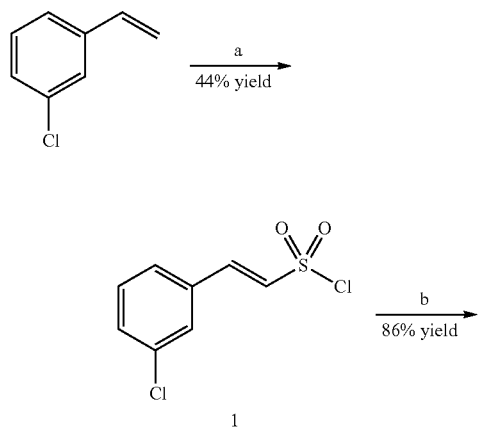

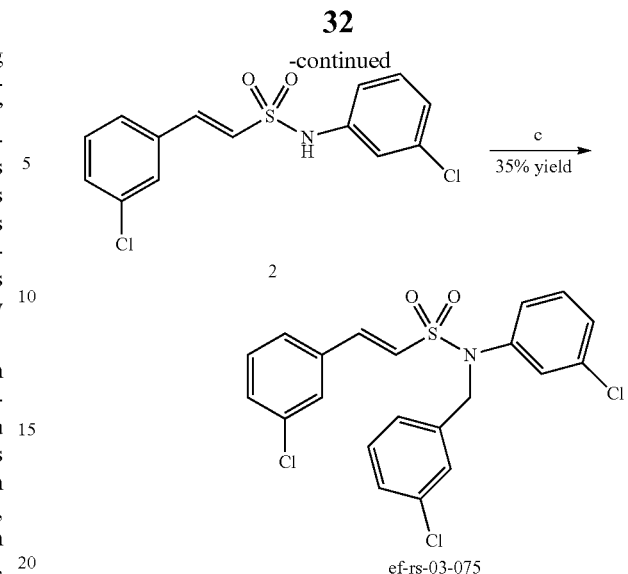

Reagents and conditions: (a) SO$_2$Cl$_2$, DMF, 55° C., 5 h (b) 3-chloroaniline, 1M Na$_2$CO$_3$, THF—H$_2$O, rt, 22 h (c) NaH, 3-chlorobenzylbromide, THF, 0° C. to rt, 22 h.

The synthesis of ef-rs-03-075 involves a three-step linear procedure. The initial step comprised the formation of ethenesulfonyl chloride 1, which was formed after heating a DMF solution of 3-chlorostyrene with sulfuryl chloride. The synthesis of ethenesulfonamide 2 involved the reaction of 3-chloroaniline with ethenesulfonyl chloride 1 using Na$_2$CO$_3$ as the base. Finally, alkylation of ethenesulfonamide 2 with 3-chlorobenzyl bromide using NaH as the base afforded the target compound ef-rs-03-075 in a 35% yield.

(E)-2-(3-chlorophenyl)ethenesulfonyl chloride (1): Sulfuryl chloride (3.2 mL, 38.5 mmol, 2 eq.) was added dropwise into a 2-neck mL round-bottomed flask containing 2.7 mL of DMF at 0° C. After stirring the mixture at room temperature for 30 min, 1-chloro-3-vinylbenzene (2.5 mL, 19.3 mmol, 1 eq.) was added and the reaction mixture was heated at 55° C. for 5 h. After the reaction mixture was cooled at room temperature, ice water was poured (20 mL) and the product was extracted three times from the aqueous phase with DCM. The resulting organic phase was washed once with water, brine and dried under Na$_2$SO$_4$. After the product was purified from the crude by flash column chromatography (5% EtOAc/hexanes), compound 1 (1.9785 g, 19.3 mmol) was obtained in a 44% yield. $^1$H NMR (400 MHz, CDCl$_3$) δ 7.67 (d, J=15.2 Hz, C=C$\underline{H}$, 1H), 7.55 (s, Ar$\underline{H}$, 1H), 7.50 (dt, J=6.4, 2.2 Hz, Ar$\underline{H}$, 1H), 7.46-7.40 (m, Ar$\underline{H}$, 2H), 7.25 (d, J=15.1 Hz, C=C$\underline{H}$, 1H). APT (100 MHz, CDCl$_3$, δ): 143.47 (C=$\underline{C}_8$H), 135.59 (C$_5$), 132.48 (C=$\underline{C}_9$H), 132.34 (C$_3$), 131.19 ($\underline{C}_1$H), 130.71 ($\underline{C}_2$H), 128.77 ($\underline{C}_4$H), 127.40 ($\underline{C}_6$H). GC-MS m/z (% relative intensity, ion): 239.95 (2, M+4), 237.95 (13, M+2), 235.95 (19, M$^+$), 201 (35, M$^+$-Cl), 137 (100, M$^+$-SO$_2$Cl), 102(85), 75 (45), 51 (28). HPLC: 99.7% pure, retention time 4.98 min.

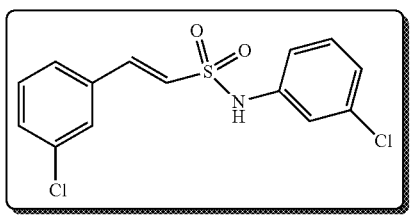

(E)-N,2-bis(3-chlorophenyl)ethenesulfonamide (2): To a well-stirred solution of 3-chloroaniline (367.9 mg, 2.87 mmol, 1 eq.) in a solvent system of $H_2O$-THF (14 mL, 1:1 ratio) was sequentially added first compound 1 (676.6 mg, 2.87 mmol, 1 eq.) and then a 1M-solution of $Na_2CO_3$ (2.2 mL, 0.77 mmol, 0.77 eq.) until the pH was about 8. After the reaction mixture was stirred for 22 hours at room temperature, water was added and the product was extracted 3 times with EtOAc from the aqueous phase. The resulting organic phase was washed with brine, dried under $Na_2SO_4$ and the solvent evaporated. After the product was purified from the crude by flash column chromatography (10% EtOAc/hexanes), compound 2 (808.5 mg, 2.46 mmol) was obtained in an 86% yield. $^1$H NMR (400 MHz, $CDCl_3$) δ 7.48 (d, J=15.4 Hz, C=C$\underline{H}$, 1H), 7.43 (s, Ar$\underline{H}$, 1H), 7.39 (dt, J=6.8, 2.3 Hz, Ar$\underline{H}$, 1H), 7.33 (m, Ar$\underline{H}$, 2H), 7.25 (t, J=8.0, Ar$\underline{H}$, 1H), 7.22 (t, J=2.1, Ar$\underline{H}$, 1H), 7.13 (ddd, J=8.0, 1.9, 0.9 Hz, Ar$\underline{H}$, 1H), 7.07 (ddd, J=8.0, 2.1, 0.9 Hz, Ar$\underline{H}$, 1H), 6.79 (d, J=15.4 Hz, C=C$\underline{H}$, 1H), 6.61 (s, N$\underline{H}$, 1H). $^{13}$C NMR (100 MHz, $CDCl_3$, δ): 142.03 (C$\underline{H}$), 137.53 (C), 135.17 (C), 133.76 (C), 131.14 (C$\underline{H}$), 130.55 (C$\underline{H}$), 130.36 (C$\underline{H}$), 128.11 (C$\underline{H}$), 126.67 (C$\underline{H}$), 125.38 (C$\underline{H}$), 125.30 (C$\underline{H}$), 120.49 (C$\underline{H}$), 118.46 (C$\underline{H}$). GC-MS m/z (% relative intensity, ion): 330.85 (0.8, M+4), 328.95 (4, M+2), 326.90 (6, M$^+$), 262.95 (28), 151.95 (48), 136.95 (99), 126.95 (54), 102.00 (100), 98.80 (51), 90.95 (19).

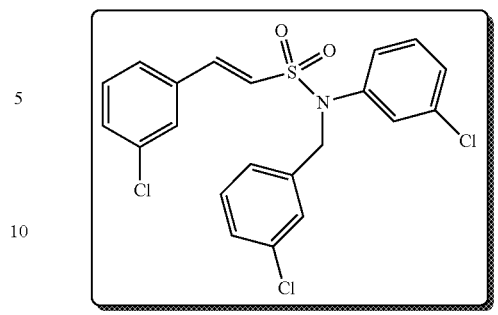

(E)-N-(3-chlorobenzyl)-N,2-bis(3-chlorophenyl)ethenesulfonamide (ef-rs-03-075): To a well-stirred suspension of NaH (23.2 mg, 0.92 mmol, 5.6 eq.) in 4 mL of THF, a THF solution (1.5 mL) of compound 2 (53.9 mg, 0.16 mmol, 1 eq.) was added and the mixture was stirred for 1 hour at room temperature. Afterwards, the reaction mixture was cooled at 0° C. and a THF solution (1.5 mL) of 3-chlorobenzylbromide (52.2 mg, 0.25 mmol, 1.5 eq.) was added. After the reaction mixture was stirred at room temperature for 22 h, water was added and the product was extracted three times from the aqueous phase with EtOAc. The resulting organic phase was washed with brine, dried under $Na_2SO_4$ and the solvent evaporated. After the product was purified from the crude by flash column chromatography (15% EtOAc/hexanes), compound ef-rs-03-075 (26.1 mg, 0.06 mmol) was obtained in a 35% yield. $^1$H NMR (400 MHz, $CDCl_3$) δ 7.46 (s, Ar$\underline{H}$, 1H), 7.42 (dt, J=7.6, 1.7 Hz, Ar$\underline{H}$, 1H), 7.36 (m, Ar$\underline{H}$, 3H), 7.23 (m, Ar$\underline{H}$, 6H), 7.14 (m, Ar$\underline{H}$, 2H), 6.78 (d, J=15.4 Hz, C=C$\underline{H}$, 1H), 4.76 (s, C$\underline{H}_2$, 2H). $^{13}$C NMR (100 MHz, $CDCl_3$, δ): 141.55 (C$\underline{H}$), 140.00 (C), 137.62 (C), 135.26 (C), 134.81 (C), 134.51 (C), 134.14 (C), 131.04 (C$\underline{H}$), 130.45 (C$\underline{H}$), 130.24 (C$\underline{H}$), 129.92 (C$\underline{H}$), 128.91 (C$\underline{H}$), 128.56 (C$\underline{H}$), 128.49 (C$\underline{H}$), 128.27 (C$\underline{H}$), 127.97 (C$\underline{H}$), 127.03 (C$\underline{H}$), 126.59 (C$\underline{H}$), 126.55 (C$\underline{H}$), 124.48 (C$\underline{H}$), 54.36 (C$\underline{H}_2$).

Example 2

TABLE 1

INHIBITION OF CHYMASE AND RELATED SERINE PROTEASES

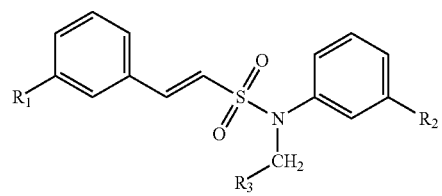

| Compound | $R_1$ | $R_2$ | $R_3$ | Chymase Ki [nM] | Selectivity of chymase inhibitors[a] | | | |
|---|---|---|---|---|---|---|---|---|
| | | | | | DPPIV | Thrombin | Trypsin | Tryptase |
| ef-rs-08-051 | Cl | Cl | 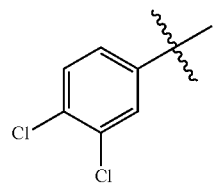 [SMILES: *c1ccc(Cl)c(Cl)c1] | 903 ± 150 | 16 | 70 | >120 | >110 |

TABLE 1-continued
INHIBITION OF CHYMASE AND RELATED SERINE PROTEASES
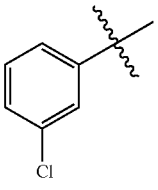 [SMILES: *c1cccc(Cl)c1]
| Compound | $R_1$ | $R_2$ | $R_3$ | Chymase Ki [nM] | Selectivity of chymase inhibitors[a] | | | |
|---|---|---|---|---|---|---|---|---|
| | | | | | DPPIV | Thrombin | Trypsin | Tryptase |
| ef-rs-03-075 | Cl | Cl | 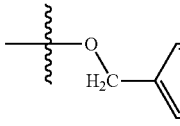 | 959 ± 42 | 37 | >320 | >110 | >410 |
| ef-rs-08-052 | Cl | 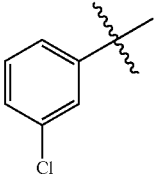 [SMILES: *c1cccc(Cl)c1] | 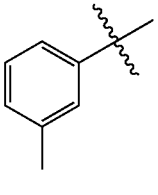 [SMILES: *c1cccc(C)c1] | 978 ± 87 | 10 | >75 | >110 | >100 |
| ef-rs-08-049 | Cl | Cl | 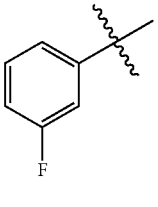 [SMILES: *c1cccc(F)c1] | 1110 ± 220 | 170 | 13 | >100 | >350 |
| ef-rs-08-057 | Cl | Cl | 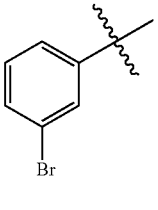 [SMILES: *c1cccc(Br)c1] | 1190 ± 120 | 70 | >50 | >100 | >80 |
| ef-rs-08-050 | Cl | Cl | 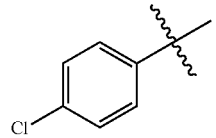 [SMILES: *c1ccc(Cl)cc1] | 1220 ± 190 | 40 | 45 | >90 | >320 |
| ef-rs-08-056 | Cl | Cl | 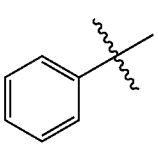 [SMILES: *c1ccccc1] | 1260 ± 200 | 80 | 20 | >85 | >310 |
| ef-rs-03-019-P4 | Cl | Cl |  | 1320 ± 280 | >100 | >200 | 11 | >275 |

TABLE 1-continued

INHIBITION OF CHYMASE AND RELATED SERINE PROTEASES

| Compound | $R_1$ | $R_2$ | $R_3$ | Chymase Ki [nM] | DPPIV | Thrombin | Trypsin | Tryptase |
|---|---|---|---|---|---|---|---|---|
| ef-rs-03-039-P1 | Br | Cl | (3-thienyl) | 1340 ± 390 | 17 | >60 | 37 | >310 |
| ef-rs-03-038-P1 | Cl | Cl | (3-thienyl) | 1570 ± 390 | 34 | >60 | 12 | >240 |
| ef-rs-03-015-P2 | Br | Cl | (phenyl) | 1580 ± 130 | >100 | >200 | 15 | >260 |

$^a$Selectivity is calculated as the ratio of $K_i$ enzyme/$K_i$ chymase

Example 3

Human Chymase Inhibition by ef-rs-03-075

A representative example of human chymase inhibition by ef-rs-03-075 is shown in FIG. 3. Further, as shown in FIG. 4, Lineweaver-Burk double reciprocal plots demonstrate the competitive inhibitory mechanism of ef-rs-03-075. As provided in Table 1, hereinabove in Example 2, selectivity was tested by measuring the inhibitory activity of ef-rs-03-075 and analogs against other serine proteases, including thrombin, trypsin, and tryrptase.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

Takai S, Jin D, Miyazaki M. Curr Med Chem. 2010; 17(28):3223-9;

Trivedi N N, Caughey G H. Am J Respir Cell Mol Biol. 2010; 42(3):257-67;

Caughey G H. Immunol Rev. 2007 June; 217:141-54;

Caughey G H. Adv Exp Med Biol. 2011; 716:212-34;

Takai S, Jin D, Muramatsu M, Okamoto Y, Miyazaki M. Eur J Pharmacol. 2004 Oct. 6; 501(1-3):1-8;

T. Matsumoto, A. Wada, T. Tsutamoto, M. Ohnishi, T. Isono and M. Kinoshita Circulation 2003, 107:2555-2558;

Jin, D., et al., Life Sci., 71, 437-46 (2002);

Muto T and Fukami H., Idrugs., 12, 1141-50 (2002);

Akahoshi F, Ashimori A, Sakashita H, Yoshimura T, Eda M, Imada T, Nakajima M, Mitsutomi N, Kuwahara S, Ohtsuka T, Fukaya C, Miyazaki M, Nakamura N. J Med Chem. 2001 Apr. 12; 44(8):1297-304; and Pereira et al, Journal of Molecular Biology Volume 286, Issue 1, 12 Feb. 1999, Pages 163-173

Although the foregoing subject matter has been described in some detail by way of illustration and example for purposes of clarity of understanding, it will be understood by those skilled in the art that certain changes and modifications can be practiced within the scope of the appended claims.

That which is claimed:

1. A compound selected from the group consisting of:

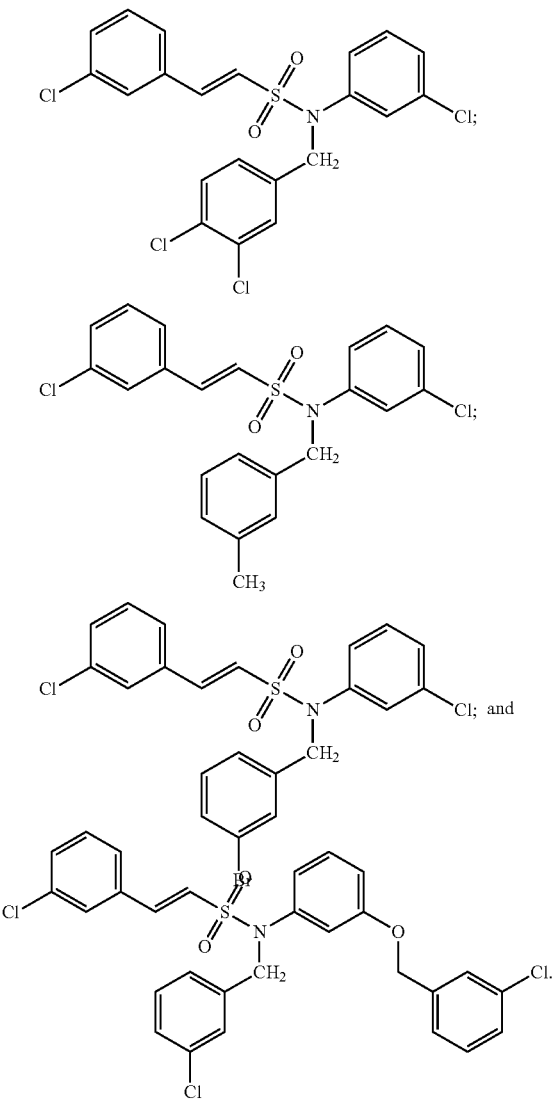

2. A pharmaceutical composition comprising a compound of claim 1.

3. A method of inhibiting a serine protease in a subject, the method comprising administering to the subject a compound of Formula (I) in an amount effective to inhibit the serine protease:

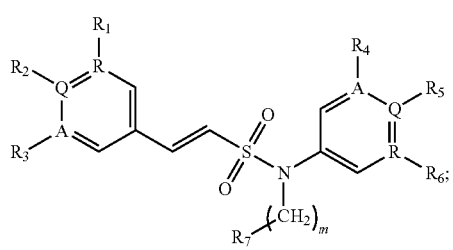
(I)

wherein:

m is an integer selected from the group consisting of 1 and 2;

A, Q, and R are each carbon;

$R_1$, $R_2$, $R_3$, $R_4$, $R_5$, $R_6$, and $R_9$ are each independently selected from the group consisting of hydrogen, substituted or unsubstituted alkyl, alkoxyl, hydroxyl, hydroxyalkyl, carboxyl, acyl, including —$COOR_{10}$, wherein $R_{10}$ is lower alkyl, carbonyl, carbamoyl, alkylcarbamoyl, halogen, amino, nitro, nitrile, amide, haloalkyl, aryl, cycloalkyl, aralkyloxyl, and —$SO_3H$;

$R_7$ is selected from the group consisting of:

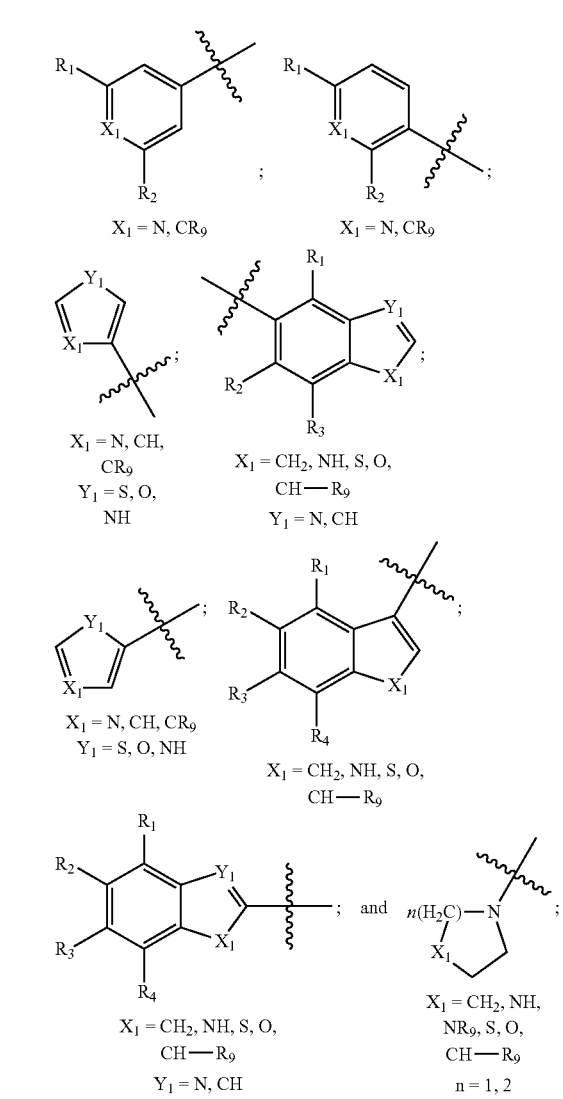

and a pharmaceutically acceptable salt, or solvate thereof.

4. The method of claim 3, wherein $R_1$-$R_6$ and are each independently selected from the group consisting of t-butyl, Cl, Br, methyl, —$OCH_3$, —$NO_2$, —$NH_2$, —OH, —$CH_2OH$, —CHO, —COOH, —$COOCH_3$, —$COOCH_2CH_3$, —$CF_3$, —$CONHCH_3$, —C≡N, —$CONH_2$, H, F, isopropyl, phenyl, cyclohexyl, benzyloxyl, and —$SO_3H$.

5. The method of claim 3, wherein the compound of Formula (I) is selected from the group consisting of:

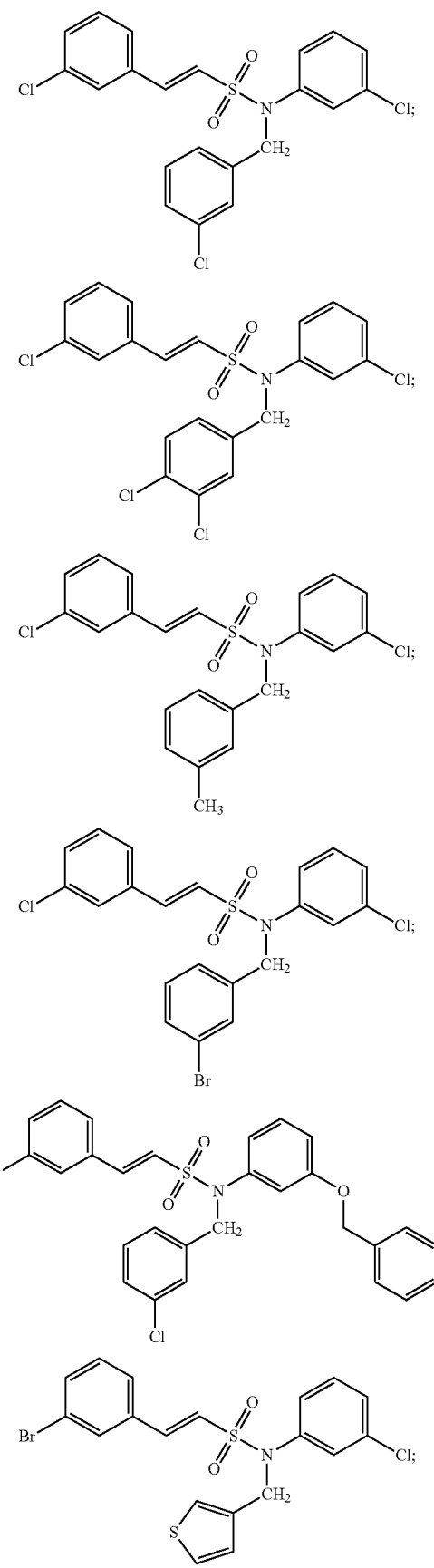

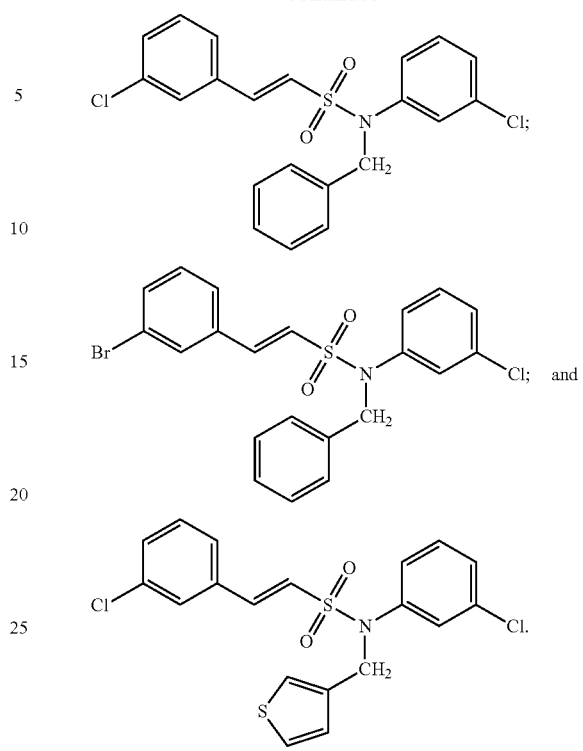

6. The method of claim 3, wherein the serine protease is selected from the group consisting of chymase, trypsin, tryptase, chymotrypsin, elastase, thrombin, plasmin, kallikrein, Complement C1, acrosomal protease, lysosomal protease, cocoonase, α-lytic protease, protease A, protease B, serine carboxypeptidase II, subtilisin, urokinase, Factor VIIa, Factor IXa, and Factor Xa.

7. The method of claim 6, wherein the serine protease is chymase.

8. A method for treating a serine protease-associated disease in a subject in need of treatment thereof, the method comprising administering to the subject a therapeutically-effective amount of a compound of Formula (I):

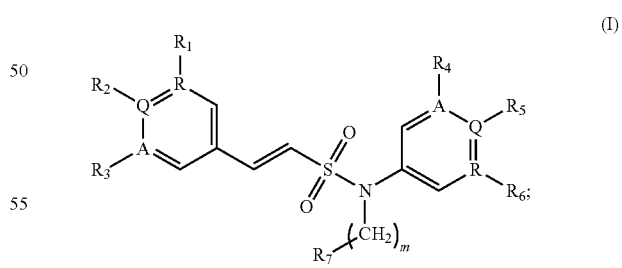

wherein:

m is an integer selected from the group consisting of 1 and 2;

A, Q, and R are carbon;

$R_1$, $R_2$, $R_3$, $R_4$, $R_5$, $R_6$, and $R_9$ are each independently selected from the group consisting of hydrogen, substituted or unsubstituted alkyl, alkoxyl, hydroxyl, hydroxyalkyl, carboxyl, acyl, including —COOR$_{10}$, wherein R$_{10}$ is lower alkyl, carbonyl, carbamoyl, alkylcarbamoyl, halogen, amino, nitro, nitrile, amide, haloalkyl, aryl, cycloalkyl, aralkyloxyl, and —SO$_3$H;

R$_7$ is selected from the group consisting of:

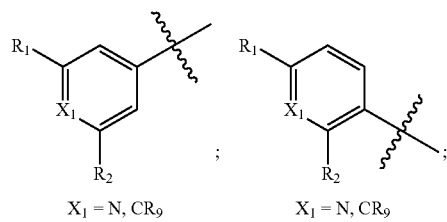

X$_1$ = N, CR$_9$   X$_1$ = N, CR$_9$

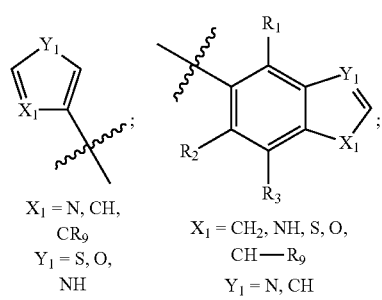

X$_1$ = N, CH, CR$_9$
Y$_1$ = S, O, NH

X$_1$ = CH$_2$, NH, S, O, CH—R$_9$
Y$_1$ = N, CH

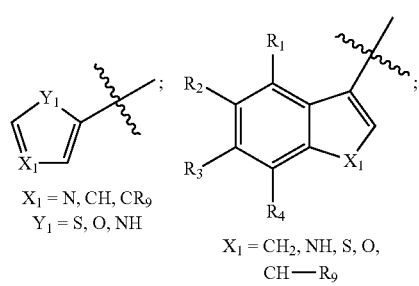

X$_1$ = N, CH, CR$_9$
Y$_1$ = S, O, NH

X$_1$ = CH$_2$, NH, S, O, CH—R$_9$
Y$_1$ = N, CH

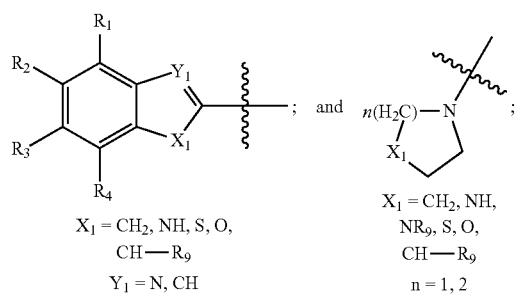

and

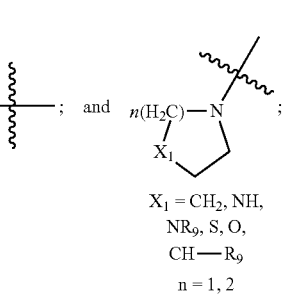

X$_1$ = CH$_2$, NH, S, O, CH—R$_9$
Y$_1$ = N, CH

X$_1$ = CH$_2$, NH, NR$_9$, S, O, CH—R$_9$
n = 1, 2 and a pharmaceutically acceptable salt, or solvate thereof.

9. The method of claim 8, wherein R$_1$-R$_6$ are each independently selected from the group consisting of t-butyl, Cl, Br, methyl, —OCH$_3$, —NO$_2$, —NH$_2$, —OH, —CH$_2$OH, —CHO, —COOH, —COOCH$_3$, —COOCH$_2$CH$_3$, —CF$_3$, —CONHCH$_3$, —C≡N, —CONH$_2$, H, F, isopropyl, phenyl, cyclohexyl, benzyloxyl, and —SO$_3$H.

10. The method of claim 8, wherein the compound of Formula (I) is selected from the group consisting of:

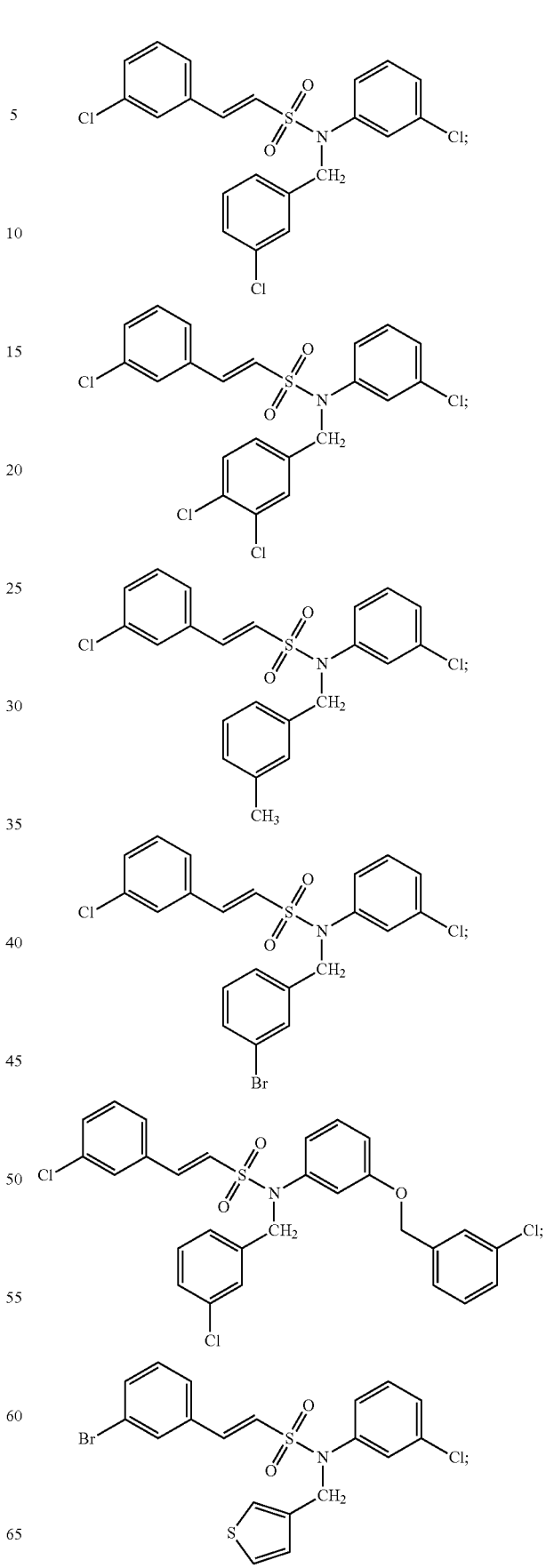

-continued

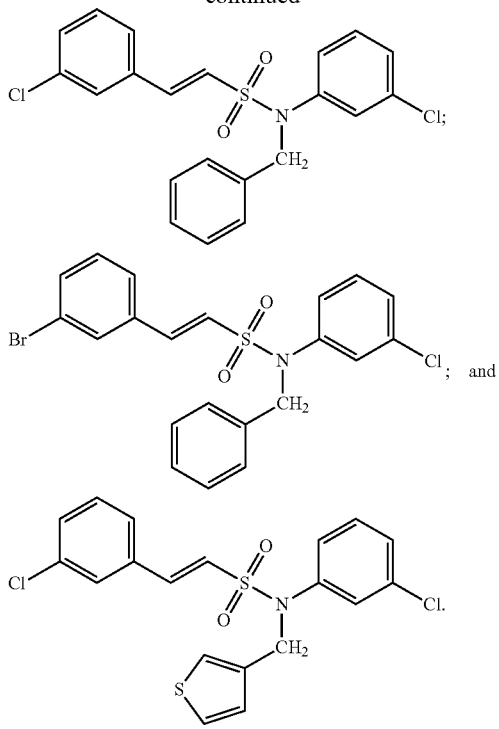

11. The method of claim 8, wherein the serine protease-associated disease is a chymase-associated disease.

12. The method of claim 11, wherein the chymase-associated disease is selected from the group consisting of asthma, allergic rhinitis, fibrosis, hypertension, cardiac hypertrophy, heart failure, rheumatoid arthritis, diabetic nephropathy, chronic obstructive pulmonary disease (COPD), an inflammatory disease, urticaria, atopic dermatitis, allergic conjunctivitis, mastocytosis, scleroderma, atherosclerosis, myocardial ischemia, myocardial infarction, restenosis after percutaneous transluminal coronary angioplasty (PTCA), restenosis after bypass graft surgery, ischemic peripheral circulatory disorders, hyperaldosteronism, diabetic retinopathy, nephritis, glomerulosclerosis, renal insufficiency, psoriasis, solid tumor, postoperative adhesion, glaucoma, ocular hypertension, hypercardia, diabetic or non-diabetic renal disease, ischemic re-perfusion disorder, keloid, psoriasis, solid tumors, and pulmonary hypertension.

13. The method of claim 11, wherein the chymase-associated disease comprises a cardiovascular disease.

14. The method of claim 13, wherein the cardiovascular disease comprises a cardiac or circulatory system disease due to abnormal exacerbation of angiotensin II (Ang II) production.

15. The method of claim 13, wherein the cardiovascular disease is selected from the group consisting of cardiac insufficiency, hypercardia, a stasis cardiac disease, hypertension, arteriosclerosis, a peripheral circulatory disorder, revasoconstriction after PCTA, a diabetic renal disorder, a non-diabetic renal disorders, myocardial infarction, angioendothelia, vascular disorders accompanying arterialization or atheroma, and a repair of organs affected by stroke.

16. The method of claim 8, further comprising administering a second therapeutic agent in combination with the compound of Formula (I).

17. The method of claim 16, wherein the second therapeutic agent is selected from the group consisting of an angiotensin I-converting enzyme (ACE) inhibitor, an alpha-adrenergic blocker, a central adrenergic inhibitor, a beta-adrenergic blocker, an angiotensin II receptor blocker, a calcium channel blocker, a vasodilator, a phosphodiesterase (PDE) inhibitor, an HMG-CoA reductase inhibitor, a cholesterol-lowering agent, an antiarrhythmic agent, a digitalis drug, a nitrate, a diuretic, an anticoagulant, an antiplatelet, a thrombolytic agent, and combinations thereof.

18. The method of claim 16, wherein the second therapeutic agent is selected from the group consisting of a CETP inhibitor/apoA1 mimetic, an adenosine diphosphate (P2Y12) inhibitor, an aldosterone antagonist, a factor Xa inhibitor, a natriuretic peptide (ANP/BNP), a renin inhibitor, a Rho kinase inhibitor, a Lipoprotein-associated phospholipase A2 inhibitor, a cardiac glycoside, a fibrate, an Endothelin Receptor Antagonist, a GPIIb/IIIa inhibitor, a histone deacetylase inhibitor, a nicotinic acid derivative, a vasopeptidase inhibitor, a nitrite, a fatty acid oxidation inhibitor, an acyl-CoA: cholesterol acyltransferase inhibitor, a microsomal triglyceride transfer protein inhibitor, a thiazolidinedione, a adenosine receptor modulator, a cholesterol absorbtion inhibitor, an Advanced Glycation End product/receptor (AGE/RAGE) interaction modulator/blocker, a dipyridamole, a gene therapy, a cell therapy, and combinations thereof.

19. The method of claim 16, wherein the second therapeutic agent is administered sequentially, simultaneously, or a combination thereof, with a compound of Formula (I).

* * * * *

UNITED STATES PATENT AND TRADEMARK OFFICE
CERTIFICATE OF CORRECTION

PATENT NO. : 9,371,307 B2
APPLICATION NO. : 14/344450
DATED : June 21, 2016
INVENTOR(S) : Ernesto Freire, Patrick C. Ross and Rogelio Siles Page 1 of 1

It is certified that error appears in the above-identified patent and that said Letters Patent is hereby corrected as shown below:

In the Specification

Column 1 Line 16 insert:
--STATEMENT OF GOVERNMENTAL INTEREST
This invention was made with government support under GM057144, awarded by the National Institutes of Health. The government has certain rights in the invention.--

Signed and Sealed this
First Day of June, 2021

Drew Hirshfeld
*Performing the Functions and Duties of the*
*Under Secretary of Commerce for Intellectual Property and*
*Director of the United States Patent and Trademark Office*